US012642935B2

(12) United States Patent
Kooij et al.

(10) Patent No.: US 12,642,935 B2
(45) Date of Patent: Jun. 2, 2026

(54) THERAPY SYSTEM FOR RESPIRATORY-RELATED DISORDERS, AND PATIENT INTERFACE AND HEADGEAR FOR USE IN SAME

(71) Applicants: RESMED PTY LTD, Bella Vista (AU); RESMED ASIA PTE. LTD., Singapore (SG)

(72) Inventors: Michiel Kooij, Sydney (AU); Adam Francis Barlow, Sydney (AU); Iain McNicol Finlay, Sydney (AU); Robin Yew, Singapore (SG); Muhammad Adil Bin Abdul Halim, Singapore (SG)

(73) Assignee: ResMed Pty Ltd., Bella Vista (AU)

( * ) Notice: Subject to any disclaimer, the term of this patent is extended or adjusted under 35 U.S.C. 154(b) by 1098 days.

(21) Appl. No.: 17/642,149

(22) PCT Filed: Sep. 10, 2020

(86) PCT No.: PCT/AU2020/050962

§ 371 (c)(1),
(2) Date: Mar. 10, 2022

(87) PCT Pub. No.: WO2021/046608

PCT Pub. Date: Mar. 18, 2021

(65) Prior Publication Data

US 2022/0379061 A1 Dec. 1, 2022

(30) Foreign Application Priority Data

Sep. 10, 2019 (AU) ................................ 2019903364
Sep. 10, 2019 (AU) ................................ 2019903366

(51) Int. Cl.
*A61M 16/06* (2006.01)
*A61M 16/08* (2006.01)

(52) U.S. Cl.
CPC .... *A61M 16/0683* (2013.01); *A61M 16/0611* (2014.02); *A61M 16/0672* (2014.02); *A61M 16/0816* (2013.01)

(58) Field of Classification Search
CPC .. A61M 16/00; A61M 16/06; A61M 16/0605; A61M 16/0611; A61M 16/0616;
(Continued)

(56) References Cited

U.S. PATENT DOCUMENTS 4,782,832 A 11/1988 Trimble et al.
4,944,310 A 7/1990 Sullivan
(Continued)

FOREIGN PATENT DOCUMENTS

WO WO 98/004310 A1 2/1998
WO WO 98/034665 A1 8/1998
(Continued)

OTHER PUBLICATIONS

"*Respiratory Physiology*", by John B. West, Lippincott Williams & Wilkins, 9th edition published 2012 (8 pages).
(Continued)

*Primary Examiner* — Colin W Stuart
(74) *Attorney, Agent, or Firm* — Nixon & Vanderhye P.C.

(57) ABSTRACT

A patient interface for delivery of a flow of pressurised air to an entrance of a patient's airways includes a mask with a seal-forming structure and one or more positioning and stabilising structures to provide a force to hold the mask in a therapeutically effective position on the patient's head. The patient interface may also include more than one connection port arranged to receive an end of an air circuit for delivering the flow of pressurised air to the seal-forming structure. The patient may connect the air circuit to a connection port of choice, depending on whether it is desired to have the end
(Continued)

of the air circuit positioned superior to the patient's otobasion superior or inferior to the patient's otobasion superior.

43 Claims, 21 Drawing Sheets

(58) Field of Classification Search
CPC .......... A61M 16/0622; A61M 16/0633; A61M 16/0638; A61M 16/0644; A61M 16/065; A61M 16/0655; A61M 16/0683; A61M 2016/0661; A61M 2210/0662
See application file for complete search history.

(56) References Cited

U.S. PATENT DOCUMENTS

| | | | | |
|---|---|---|---|---|
| 5,538,000 | A * | 7/1996 | Rudolph | A61M 16/0672 128/207.18 |
| 6,532,959 | B1 | 3/2003 | Berthon-Jones | |
| 6,581,594 | B1 | 6/2003 | Drew et al. | |
| 7,866,944 | B2 | 1/2011 | Kenyon et al. | |
| 7,931,023 | B2 * | 4/2011 | Berthon-Jones | A61M 16/06 128/204.21 |
| 8,636,479 | B2 | 1/2014 | Kenyon et al. | |
| 8,638,014 | B2 | 1/2014 | Sears et al. | |
| 8,733,349 | B2 | 5/2014 | Bath et al. | |
| 9,937,312 | B2 * | 4/2018 | Kwok | A61M 16/0683 |
| 2004/0226566 | A1 | 11/2004 | Gunaratnam et al. | |
| 2007/0246043 | A1 | 10/2007 | Kwok et al. | |
| 2009/0044808 | A1 | 2/2009 | Guney et al. | |
| 2009/0050156 | A1 | 2/2009 | Ng et al. | |
| 2009/0107508 | A1 * | 4/2009 | Brambilla | A61M 16/0644 128/207.11 |
| 2010/0000534 | A1 | 1/2010 | Kooij et al. | |
| 2010/0018534 | A1 | 1/2010 | Veliss et al. | |
| 2011/0240031 | A1 | 10/2011 | Jaffre et al. | |
| 2013/0131534 | A1 | 5/2013 | Heatherington et al. | |
| 2013/0133646 | A1 | 5/2013 | Rose et al. | |
| 2015/0128952 | A1 | 5/2015 | Matula, Jr. et al. | |
| 2016/0271354 | A1 | 9/2016 | Grashow et al. | |
| 2017/0151409 | A1 | 6/2017 | Peacock et al. | |
| 2017/0274167 | A1 | 9/2017 | Huddart et al. | |
| 2017/0304574 | A1 | 10/2017 | Mcauley et al. | |
| 2017/0312468 | A1 * | 11/2017 | Formica | A61M 16/0622 |
| 2018/0071475 | A1 | 3/2018 | Howard et al. | |
| 2018/0126102 | A1 * | 5/2018 | Guney | A61M 16/0683 |
| 2018/0207385 | A1 | 7/2018 | Freestone et al. | |
| 2019/0117928 | A1 | 4/2019 | Gunarathnam et al. | |
| 2019/0269870 | A1 | 9/2019 | Kwok et al. | |

FOREIGN PATENT DOCUMENTS

| | | | | |
|---|---|---|---|---|
| WO | WO 2000/078381 | A1 | 12/2000 | |
| WO | WO 2004/073778 | A1 | 9/2004 | |
| WO | WO 2005/063328 | A1 | 7/2005 | |
| WO | WO 2006/074513 | A1 | 7/2006 | |
| WO | WO 2006/130903 | A1 | 12/2006 | |
| WO | WO 2009/052560 | A1 | 4/2009 | |
| WO | WO 2010/135785 | A1 | 12/2010 | |
| WO | WO-2010139014 | A1 * | 12/2010 | A61M 16/0616 |
| WO | WO 2012/171072 | A1 | 12/2012 | |
| WO | WO 2013/020167 | A1 | 2/2013 | |

OTHER PUBLICATIONS

International Search Report for International Appln. No. PCT/AU2020/050962 issued Dec. 1, 2020 (16 pages).
Written Opinion of the ISA for International Appln. No. PCT/AU2020/050962 issued Dec. 1, 2020 (7 pages).
Written Opinion of the IPEA for International Appln No. PCT/AU2020/050962 issued Aug. 16, 2021 (4 pages).
First Office Action issued in corresponding Chinese Patent Application No. 202080076160.8, dated Jun. 27, 2025 (17 pages).

* cited by examiner

THERAPY SYSTEM FOR RESPIRATORY-RELATED DISORDERS, AND PATIENT INTERFACE AND HEADGEAR FOR USE IN SAME

1 CROSS-REFERENCE TO RELATED APPLICATIONS

This application is the U.S. national phase of International Application No. PCT/AU2020/050962 filed Sep. 10, 2020 which designated the U.S. and claims priority to Australian Provisional Application No. 2019903366 filed Sep. 10, 2019, and Australian Provisional Application No. 2019903364 filed Sep. 10, 2019, the entire contents of each of which are hereby incorporated by reference.

2 BACKGROUND OF THE TECHNOLOGY

2.1.1 Field of the Technology

The present technology relates to one or more of the screening, diagnosis, monitoring, treatment, prevention and amelioration of respiratory-related disorders. The present technology also relates to medical devices or apparatus, and their use.

2.2 Description of the Related Art

2.2.1 Human Respiratory System and its Disorders

The respiratory system of the body facilitates gas exchange. The nose and mouth form the entrance to the airways of a patient.

The airways include a series of branching tubes, which become narrower, shorter and more numerous as they penetrate deeper into the lung. The prime function of the lung is gas exchange, allowing oxygen to move from the inhaled air into the venous blood and carbon dioxide to move in the opposite direction. The trachea divides into right and left main bronchi, which further divide eventually into terminal bronchioles. The bronchi make up the conducting airways, and do not take part in gas exchange. Further divisions of the airways lead to the respiratory bronchioles, and eventually to the alveoli. The alveolated region of the lung is where the gas exchange takes place, and is referred to as the respiratory zone. See "*Respiratory Physiology*", by John B. West, Lippincott Williams & Wilkins, 9th edition published 2012.

A range of respiratory disorders exist. Certain disorders may be characterised by particular events, e.g. apneas, hypopneas, and hyperpneas.

Examples of respiratory disorders include Obstructive Sleep Apnea (OSA), Cheyne-Stokes Respiration (CSR), respiratory insufficiency, Obesity Hyperventilation Syndrome (OHS), Chronic Obstructive Pulmonary Disease (COPD), Neuromuscular Disease (NMD) and Chest wall disorders.

Obstructive Sleep Apnea (OSA), a form of Sleep Disordered Breathing (SDB), is characterised by events including occlusion or obstruction of the upper air passage during sleep. It results from a combination of an abnormally small upper airway and the normal loss of muscle tone in the region of the tongue, soft palate and posterior oropharyngeal wall during sleep. The condition causes the affected patient to stop breathing for periods typically of 30 to 120 seconds in duration, sometimes 200 to 300 times per night. It often causes excessive daytime somnolence, and it may cause cardiovascular disease and brain damage. The syndrome is a common disorder, particularly in middle aged overweight males, although a person affected may have no awareness of the problem. See U.S. Pat. No. 4,944,310 (Sullivan).

Cheyne-Stokes Respiration (CSR) is another form of sleep disordered breathing. CSR is a disorder of a patient's respiratory controller in which there are rhythmic alternating periods of waxing and waning ventilation known as CSR cycles. CSR is characterised by repetitive de-oxygenation and re-oxygenation of the arterial blood. It is possible that CSR is harmful because of the repetitive hypoxia. In some patients CSR is associated with repetitive arousal from sleep, which causes severe sleep disruption, increased sympathetic activity, and increased afterload. See U.S. Pat. No. 6,532,959 (Berthon-Jones).

Respiratory failure is an umbrella term for respiratory disorders in which the lungs are unable to inspire sufficient oxygen or exhale sufficient $CO_2$ to meet the patient's needs. Respiratory failure may encompass some or all of the following disorders.

A patient with respiratory insufficiency (a form of respiratory failure) may experience abnormal shortness of breath on exercise.

Obesity Hyperventilation Syndrome (OHS) is defined as the combination of severe obesity and awake chronic hypercapnia, in the absence of other known causes for hypoventilation. Symptoms include dyspnea, morning headache and excessive daytime sleepiness.

Chronic Obstructive Pulmonary Disease (COPD) encompasses any of a group of lower airway diseases that have certain characteristics in common. These include increased resistance to air movement, extended expiratory phase of respiration, and loss of the normal elasticity of the lung. Examples of COPD are emphysema and chronic bronchitis. COPD is caused by chronic tobacco smoking (primary risk factor), occupational exposures, air pollution and genetic factors. Symptoms include: dyspnea on exertion, chronic cough and sputum production.

Neuromuscular Disease (NMD) is a broad term that encompasses many diseases and ailments that impair the functioning of the muscles either directly via intrinsic muscle pathology, or indirectly via nerve pathology. Some NMD patients are characterised by progressive muscular impairment leading to loss of ambulation, being wheelchair-bound, swallowing difficulties, respiratory muscle weakness and, eventually, death from respiratory failure. Neuromuscular disorders can be divided into rapidly progressive and slowly progressive: (i) Rapidly progressive disorders: Characterised by muscle impairment that worsens over months and results in death within a few years (e.g. Amyotrophic lateral sclerosis (ALS) and Duchenne muscular dystrophy (DMD) in teenagers); (ii) Variable or slowly progressive disorders: Characterised by muscle impairment that worsens over years and only mildly reduces life expectancy (e.g. Limb girdle, Facioscapulohumeral and Myotonic muscular dystrophy). Symptoms of respiratory failure in NMD include: increasing generalised weakness, dysphagia, dyspnea on exertion and at rest, fatigue, sleepiness, morning headache, and difficulties with concentration and mood changes.

Chest wall disorders are a group of thoracic deformities that result in inefficient coupling between the respiratory muscles and the thoracic cage. The disorders are usually characterised by a restrictive defect and share the potential of long term hypercapnic respiratory failure. Scoliosis and/or kyphoscoliosis may cause severe respiratory failure. Symptoms of respiratory failure include: dyspnea on exertion, peripheral oedema, orthopnea, repeated chest infections, morning headaches, fatigue, poor sleep quality and loss of appetite.

A range of therapies have been used to treat or ameliorate such conditions. Furthermore, otherwise healthy individuals may take advantage of such therapies to prevent respiratory disorders from arising. However, these have a number of shortcomings.

2.2.2 Therapies

Various respiratory therapies, such as Continuous Positive Airway Pressure (CPAP) therapy, Non-invasive ventilation (NIV), Invasive ventilation (IV), and High Flow Therapy (HFT) have been used to treat one or more of the above respiratory disorders.

2.2.2.1 Respiratory Pressure Therapies

Respiratory pressure therapy is the application of a supply of air to an entrance to the airways at a controlled target pressure that is nominally positive with respect to atmosphere throughout the patient's breathing cycle (in contrast to negative pressure therapies such as the tank ventilator or cuirass).

Continuous Positive Airway Pressure (CPAP) therapy has been used to treat Obstructive Sleep Apnea (OSA). The mechanism of action is that continuous positive airway pressure acts as a pneumatic splint and may prevent upper airway occlusion, such as by pushing the soft palate and tongue forward and away from the posterior oropharyngeal wall. Treatment of OSA by CPAP therapy may be voluntary, and hence patients may elect not to comply with therapy if they find devices used to provide such therapy one or more of: uncomfortable, difficult to use, expensive and aesthetically unappealing.

Non-invasive ventilation (NIV) provides ventilatory support to a patient through the upper airways to assist the patient breathing and/or maintain adequate oxygen levels in the body by doing some or all of the work of breathing. The ventilatory support is provided via a non-invasive patient interface. NIV has been used to treat CSR and respiratory failure, in forms such as OHS, COPD, NMD and Chest Wall disorders. In some forms, the comfort and effectiveness of these therapies may be improved.

Invasive ventilation (IV) provides ventilatory support to patients that are no longer able to effectively breathe themselves and may be provided using a tracheostomy tube. In some forms, the comfort and effectiveness of these therapies may be improved.

2.2.2.2 Flow Therapies

Not all respiratory therapies aim to deliver a prescribed therapeutic pressure. Some respiratory therapies aim to deliver a prescribed respiratory volume, by delivering an inspiratory flow rate profile over a targeted duration, possibly superimposed on a positive baseline pressure. In other cases, the interface to the patient's airways is 'open' (unsealed) and the respiratory therapy may only supplement the patient's own spontaneous breathing with a flow of conditioned or enriched gas. In one example, High Flow therapy (HFT) is the provision of a continuous, heated, humidified flow of air to an entrance to the airway through an unsealed or open patient interface at a "treatment flow rate" that is held approximately constant throughout the respiratory cycle. The treatment flow rate is nominally set to exceed the patient's peak inspiratory flow rate. HFT has been used to treat OSA, CSR, respiratory failure, COPD, and other respiratory disorders. One mechanism of action is that the high flow rate of air at the airway entrance improves ventilation efficiency by flushing, or washing out, expired $CO_2$ from the patient's anatomical deadspace. Hence, HFT is thus sometimes referred to as a deadspace therapy (DST). Other benefits may include the elevated warmth and humidification (possibly of benefit in secretion management) and the potential for modest elevation of airway pressures. As an alternative to constant flow rate, the treatment flow rate may follow a profile that varies over the respiratory cycle.

Another form of flow therapy is long-term oxygen therapy (LTOT) or supplemental oxygen therapy. Doctors may prescribe a continuous flow of oxygen enriched gas at a specified oxygen concentration (from 21%, the oxygen fraction in ambient air, to 100%) at a specified flow rate (e.g., 1 litre per minute (LPM), 2 LPM, 3 LPM, etc.) to be delivered to the patient's airway.

2.2.2.3 Supplementary Oxygen

For certain patients, oxygen therapy may be combined with a respiratory pressure therapy or HFT by adding supplementary oxygen to the pressurised flow of air. When oxygen is added to respiratory pressure therapy, this is referred to as RPT with supplementary oxygen. When oxygen is added to HFT, the resulting therapy is referred to as HFT with supplementary oxygen.

2.2.3 Respiratory Therapy Systems

These respiratory therapies may be provided by a respiratory therapy system or device. Such systems and devices may also be used to screen, diagnose, or monitor a condition without treating it.

A respiratory therapy system may comprise a Respiratory Pressure Therapy Device (RPT device), an air circuit, a humidifier, a patient interface, an oxygen source, and data management.

Another form of therapy system is a mandibular repositioning device.

2.2.3.1 Patient Interface

A patient interface may be used to interface respiratory equipment to its wearer, for example by providing a flow of air to an entrance to the airways. The flow of air may be provided via a mask to the nose and/or mouth, a tube to the mouth or a tracheostomy tube to the trachea of a patient. Depending upon the therapy to be applied, the patient interface may form a seal, e.g., with a region of the patient's face, to facilitate the delivery of gas at a pressure at sufficient variance with ambient pressure to effect therapy, e.g., at a positive pressure of about 10 $cmH_2O$ relative to ambient pressure. For other forms of therapy, such as the delivery of oxygen, the patient interface may not include a seal sufficient to facilitate delivery to the airways of a supply of gas at a positive pressure of about 10 $cmH_2O$. For flow therapies such as nasal HFT, the patient interface is configured to insufflate the nares but specifically to avoid a complete seal. One example of such a patient interface is a nasal cannula.

Certain other mask systems may be functionally unsuitable for the present field. For example, purely ornamental masks may be unable to maintain a suitable pressure. Mask systems used for underwater swimming or diving may be configured to guard against ingress of water from an external higher pressure, but not to maintain air internally at a higher pressure than ambient.

Certain masks may be clinically unfavourable for the present technology e.g. if they block airflow via the nose and only allow it via the mouth.

Certain masks may be uncomfortable or impractical for the present technology if they require a patient to insert a portion of a mask structure in their mouth to create and maintain a seal via their lips.

Certain masks may be impractical for use while sleeping, e.g. for sleeping while lying on one's side in bed with a head on a pillow.

The design of a patient interface presents a number of challenges. The face has a complex three-dimensional shape. The size and shape of noses and heads varies considerably between individuals. Since the head includes bone, cartilage and soft tissue, different regions of the face respond differently to mechanical forces. The jaw or mandible may move relative to other bones of the skull. The whole head may move during the course of a period of respiratory therapy.

As a consequence of these challenges, some masks suffer from being one or more of obtrusive, aesthetically undesirable, costly, poorly fitting, difficult to use, and uncomfortable especially when worn for long periods of time or when a patient is unfamiliar with a system. Wrongly sized masks can give rise to reduced compliance, reduced comfort and poorer patient outcomes. Masks designed solely for aviators, masks designed as part of personal protection equipment (e.g. filter masks), SCUBA masks, or for the administration of anaesthetics may be tolerable for their original application, but nevertheless such masks may be undesirably uncomfortable to be worn for extended periods of time, e.g., several hours. This discomfort may lead to a reduction in patient compliance with therapy. This is even more so if the mask is to be worn during sleep.

CPAP therapy is highly effective to treat certain respiratory disorders, provided patients comply with therapy. If a mask is uncomfortable, or difficult to use a patient may not comply with therapy. Since it is often recommended that a patient regularly wash their mask, if a mask is difficult to clean (e.g., difficult to assemble or disassemble), patients may not clean their mask and this may impact on patient compliance.

While a mask for other applications (e.g. aviators) may not be suitable for use in treating sleep disordered breathing, a mask designed for use in treating sleep disordered breathing may be suitable for other applications.

For these reasons, patient interfaces for delivery of CPAP during sleep form a distinct field.

2.2.3.1.1 Seal-Forming Structure

Patient interfaces may include a seal-forming structure. Since it is in direct contact with the patient's face, the shape and configuration of the seal-forming structure can have a direct impact on the effectiveness and comfort of the patient interface.

A patient interface may be partly characterised according to the design intent of where the seal-forming structure is to engage with the face in use. In one form of patient interface, a seal-forming structure may comprise a first sub-portion to form a seal around the left naris and a second sub-portion to form a seal around the right naris. In one form of patient interface, a seal-forming structure may comprise a single element that surrounds both nares in use. Such single element may be designed to for example overlay an upper lip region and a nasal bridge region of a face. In one form of patient interface a seal-forming structure may comprise an element that surrounds a mouth region in use, e.g. by forming a seal on a lower lip region of a face. In one form of patient interface, a seal-forming structure may comprise a single element that surrounds both nares and a mouth region in use. These different types of patient interfaces may be known by a variety of names by their manufacturer including nasal masks, full-face masks, nasal pillows, nasal puffs and oro-nasal masks.

A seal-forming structure that may be effective in one region of a patient's face may be inappropriate in another region, e.g. because of the different shape, structure, variability and sensitivity regions of the patient's face. For example, a seal on swimming goggles that overlays a patient's forehead may not be appropriate to use on a patient's nose.

Certain seal-forming structures may be designed for mass manufacture such that one design fit and be comfortable and effective for a wide range of different face shapes and sizes. To the extent to which there is a mismatch between the shape of the patient's face, and the seal-forming structure of the mass-manufactured patient interface, one or both must adapt in order for a seal to form.

One type of seal-forming structure extends around the periphery of the patient interface, and is intended to seal against the patient's face when force is applied to the patient interface with the seal-forming structure in confronting engagement with the patient's face. The seal-forming structure may include an air or fluid filled cushion, or a moulded or formed surface of a resilient seal element made of an elastomer such as a rubber. With this type of seal-forming structure, if the fit is not adequate, there will be gaps between the seal-forming structure and the face, and additional force will be required to force the patient interface against the face in order to achieve a seal.

Another type of seal-forming structure incorporates a flap seal of thin material positioned about the periphery of the mask so as to provide a self-sealing action against the face of the patient when positive pressure is applied within the mask. Like the previous style of seal forming portion, if the match between the face and the mask is not good, additional force may be required to achieve a seal, or the mask may leak. Furthermore, if the shape of the seal-forming structure does not match that of the patient, it may crease or buckle in use, giving rise to leaks.

Another type of seal-forming structure may comprise a friction-fit element, e.g. for insertion into a naris, however some patients find these uncomfortable.

Another form of seal-forming structure may use adhesive to achieve a seal. Some patients may find it inconvenient to constantly apply and remove an adhesive to their face.

A range of patient interface seal-forming structure technologies are disclosed in the following patent applications, assigned to ResMed Limited: WO 1998/004,310; WO 2006/074,513; WO 2010/135,785.

One form of nasal pillow is found in the Adam Circuit manufactured by Puritan Bennett. Another nasal pillow, or nasal puff is the subject of U.S. Pat. No. 4,782,832 (Trimble et al.), assigned to Puritan-Bennett Corporation.

ResMed Limited has manufactured the following products that incorporate nasal pillows: SWIFT™ nasal pillows mask, SWIFT™ II nasal pillows mask, SWIFT™ LT nasal pillows mask, SWIFT™ FX nasal pillows mask and MIRAGE LIBERTY™ full-face mask. The following patent applications, assigned to ResMed Limited, describe examples of nasal pillows masks: International Patent Application WO2004/073,778 (describing amongst other things aspects of the ResMed Limited SWIFT™ nasal pillows), US Patent Application 2009/0044808 (describing amongst other things aspects of the ResMed Limited SWIFT™ LT nasal pillows); International Patent Applications WO 2005/063,328 and WO 2006/130,903 (describing amongst other things aspects of the ResMed Limited MIRAGE LIBERTY™ full-face mask); International Patent Application WO 2009/052,560 (describing amongst other things aspects of the ResMed Limited SWIFT™ FX nasal pillows).

It will be appreciated that the patient has a number of options available to them for the patient interface and seal-forming structure. However, it may be a significant investment for the patient to switch between these options, particularly since they may be designed to be worn with specifically designed positioning and stabilising structures.

2.2.3.1.2 Positioning and Stabilising Structure

A seal-forming structure of a patient interface used for positive air pressure therapy is subject to the corresponding force of the air pressure to disrupt a seal. Thus a variety of techniques have been used to position the seal-forming structure, and to maintain it in sealing relation with the appropriate portion of the face.

One technique in widespread usage for positioning the seal-forming structure on the patient's face is the provision of one or more straps and/or stabilising harnesses as the positioning and stabilising structure. These structures are often referred to as headgear.

The headgear can include a plurality of straps and buckles or the like which engage with the patient interface. Some examples of headgear suffer from being one or more of ill-fitting, bulky, uncomfortable and awkward to use.

2.2.3.2 Pressurised Air Conduit

In one type of treatment system, a flow of pressurised air is provided to a patient interface through a conduit or tube in an air circuit that fluidly connects to the anterior side of the patient interface so that, when the patient interface is positioned on the patient's face during use, the conduit extends out of the patient interface forwards away from the patient's face. Usually the conduit is not connected to the patient interface at any other location so the conduit hangs vertically downwards from the interface under gravity. This type of interface may sometimes be referred to as a "tube down" or an "elephant trunk" style of interface.

2.2.3.2.1 Pressurised Air Conduit Used for Positioning/Stabilising the Seal-Forming Structure An alternative type of treatment system comprises a patient interface in which a tube or substantially hollow elongate structure that delivers pressurised air to the patient's airways also functions as part of the structure that positions and stabilises the seal-forming portion of the patient interface to the appropriate part of the patient's face, e.g. the headgear. This means that the headgear forms part of the air circuit. For the purposes of this specification the terms "tube" and "conduit" should be considered to have the same meaning, unless the context clearly indicates otherwise.

This type of patient interface may be referred to as incorporating 'headgear tubing' or 'conduit headgear', these terms being understood to be interchangeable for the purposes of this specification unless the context indicates otherwise. Such patient interfaces allow the conduit in the air circuit providing the flow of pressurised air from a respiratory pressure therapy device to connect to the patient interface in a position other than in front of the patient's face. One example of such a treatment system is disclosed in US Patent Publication No. 2007/0246043, the contents of which are incorporated herein by reference, in which the conduit connects to the patient interface through a port positioned in use on top of the patient's head. This may be referred to as a "tube up" configuration.

The Philips DreamWear™ mask includes such conduit headgear/headgear tubing. The length of the DreamWear™ headgear tubes cannot be adjusted. Consequently, the DreamWear™ headgear is supplied in three different sizes to cater for different sized patient faces. Providing a greater number of different sizes may increase the complexity and cost to manufacture the headgear and may result in larger packaging. Additionally, a supply of discretely sized masks may limit the extent to which differently sized patient heads can be accommodated. There may be a greater chance of some patients being unable to achieve what they consider a comfortable fit if forced to choose between discrete sizes that are not adjustable in length.

Some patients may prefer interfaces incorporating headgear tubing as this allows the selection of a tube up configuration, avoiding a conduit connecting to the patient interface at the front of a patient's face. This can be considered to be unsightly and obtrusive. However, other patients may not find the "tube down" style of interface to be an issue.

2.2.3.3 Respiratory Pressure Therapy (RPT) Device

A respiratory pressure therapy (RPT) device may be used individually or as part of a system to deliver one or more of a number of therapies described above, such as by operating the device to generate a flow of air for delivery to an interface to the airways. The flow of air may be pressure-controlled (for respiratory pressure therapies) or flow-controlled (for flow therapies such as HFT). Thus RPT devices may also act as flow therapy devices. Examples of RPT devices include a CPAP device and a ventilator.

Air pressure generators are known in a range of applications, e.g. industrial-scale ventilation systems. However, air pressure generators for medical applications have particular requirements not fulfilled by more generalised air pressure generators, such as the reliability, size and weight requirements of medical devices. In addition, even devices designed for medical treatment may suffer from shortcomings, pertaining to one or more of: comfort, noise, ease of use, efficacy, size, weight, manufacturability, cost, and reliability.

An example of the special requirements of certain RPT devices is acoustic noise.

Table of noise output levels of prior RPT devices (one specimen only, measured using test method specified in ISO 3744 in CPAP mode at 10 $cmH_2O$).

| RPT Device name | A-weighted sound pressure level dB(A) | Year (approx.) |
|---|---|---|
| C-Series Tango ™ | 31.9 | 2007 |
| C-Series Tango ™ with Humidifier | 33.1 | 2007 |
| S8 Escape ™ II | 30.5 | 2005 |

-continued

| RPT Device name | A-weighted sound pressure level dB(A) | Year (approx.) |
|---|---|---|
| S8 Escape ™ II with H4i ™ Humidifier | 31.1 | 2005 |
| S9 AutoSet ™ | 26.5 | 2010 |
| S9 AutoSet ™ with H5i Humidifier | 28.6 | 2010 |

One known RPT device used for treating sleep disordered breathing is the S9 Sleep Therapy System, manufactured by ResMed Limited. Another example of an RPT device is a ventilator. Ventilators such as the ResMed Stellar™ Series of Adult and Paediatric Ventilators may provide support for invasive and non-invasive non-dependent ventilation for a range of patients for treating a number of conditions such as but not limited to NMD, OHS and COPD.

The ResMed Elisée™ 150 ventilator and ResMed VS III™ ventilator may provide support for invasive and non-invasive dependent ventilation suitable for adult or paediatric patients for treating a number of conditions. These ventilators provide volumetric and barometric ventilation modes with a single or double limb circuit. RPT devices typically comprise a pressure generator, such as a motor-driven blower or a compressed gas reservoir, and are configured to supply a flow of air to the airway of a patient. In some cases, the flow of air may be supplied to the airway of the patient at positive pressure. The outlet of the RPT device is connected via an air circuit to a patient interface such as those described above.

The designer of a device may be presented with an infinite number of choices to make. Design criteria often conflict, meaning that certain design choices are far from routine or inevitable. Furthermore, the comfort and efficacy of certain aspects may be highly sensitive to small, subtle changes in one or more parameters.

2.2.3.4 Air Circuit

An air circuit is a conduit or a tube constructed and arranged to allow, in use, a flow of air to travel between two components of a respiratory therapy system such as the RPT device and the patient interface. In some cases, there may be separate limbs of the air circuit for inhalation and exhalation. In other cases, a single limb air circuit is used for both inhalation and exhalation.

The air circuit may engage with a patient interface and/or seal forming structure or alternatively, when conduit headgear is being used, engage with a connection port provided to, or in fluid communication with, the conduit headgear.

2.2.3.5 Vent Technologies

Some forms of treatment systems may include a vent to allow the washout of exhaled carbon dioxide. The vent may allow a flow of gas from an interior space of a patient interface, e.g., the plenum chamber, to an exterior of the patient interface, e.g., to ambient.

The vent may comprise an orifice and gas may flow through the orifice in use of the mask. Many such vents are noisy. Others may become blocked in use and thus provide insufficient washout. Some vents may be disruptive of the sleep of a bed partner 1100 of the patient 1000, e.g. through noise or focused airflow.

ResMed Limited has developed a number of improved mask vent technologies. See International Patent Application Publication No. WO 1998/034,665; International Patent Application Publication No. WO 2000/078,381; U.S. Pat. No. 6,581,594; US Patent Application Publication No. US 2009/0050156; US Patent Application Publication No. 2009/0044808.

Table of noise of prior masks (ISO 17510-2:2007, 10 $cmH_2O$ pressure at 1 m)

| Mask name | Mask type | A-weighted sound power level dB(A) (uncertainty) | A-weighted sound pressure dB(A) (uncertainty) | Year (approx.) |
|---|---|---|---|---|
| Glue-on (*) | nasal | 50.9 | 42.9 | 1981 |
| ResCare standard (*) | nasal | 31.5 | 23.5 | 1993 |
| ResMed Mirage ™ (*) | nasal | 29.5 | 21.5 | 1998 |
| ResMed UltraMirage ™ | nasal | 36 (3) | 28 (3) | 2000 |
| ResMed Mirage Activa ™ | nasal | 32 (3) | 24 (3) | 2002 |
| ResMed Mirage Micro ™ | nasal | 30 (3) | 22 (3) | 2008 |
| ResMed Mirage ™ SoftGel | nasal | 29 (3) | 22 (3) | 2008 |
| ResMed Mirage ™ FX | nasal | 26 (3) | 18 (3) | 2010 |
| ResMed Mirage Swift ™ (*) | nasal pillows | 37 | 29 | 2004 |
| ResMed Mirage Swift ™ II | nasal pillows | 28 (3) | 20 (3) | 2005 |
| ResMed Mirage Swift ™ LT | nasal pillows | 25 (3) | 17 (3) | 2008 |
| ResMed AirFit P10 | nasal pillows | 21 (3) | 13 (3) | 2014 |

(*) one specimen only, measured using test method specified in ISO 3744 in CPAP mode at 10 $cmH_2O$)

Sound pressure values of a variety of objects are listed below:

| Object | A-weighted sound pressure dB(A) | Notes |
|---|---|---|
| Vacuum cleaner: Nilfisk Walter Broadly Litter Hog: B+ Grade | 68 | ISO 3744 at 1 m distance |
| Conversational speech | 60 | 1 m distance |
| Average home | 50 | |
| Quiet library | 40 | |
| Quiet bedroom at night | 30 | |
| Background in TV studio | 20 | |

3 BRIEF SUMMARY OF THE TECHNOLOGY

The present technology is directed towards providing medical devices used in the screening, diagnosis, monitoring, amelioration, treatment, or prevention of respiratory disorders having one or more of improved comfort, cost, efficacy, ease of use and manufacturability.

A first aspect of the present technology relates to apparatus used in the screening, diagnosis, monitoring, amelioration, treatment or prevention of a respiratory disorder.

Another aspect of the present technology relates to methods used in the screening, diagnosis, monitoring, amelioration, treatment or prevention of a respiratory disorder.

An aspect of certain forms of the present technology is to provide methods and/or apparatus that improve the compliance of patients with respiratory therapy.

One aspect of the present technology comprises a patient interface for delivery of a flow of pressurised air to an entrance of a patient's airways.

One aspect of the present technology is directed to a patient interface for delivery of a flow of pressurised air from an air circuit to an entrance of a patient's airways, the patient interface comprising:

a plenum chamber;

a seal-forming structure provided to the plenum chamber;

one or more connection ports configured to receive the flow of air from the air circuit and to deliver the flow of air to the entrance of the patient's airways via the seal-forming structure; and one or more positioning and stabilising structures configured to provide a force to hold the seal-forming structure in a therapeutically effective position on a patient's head in use, wherein the patient interface is structured and arranged to be worn by the patient in a first use configuration and a second use configuration, wherein in the first use configuration, the air circuit is connected to a connection port of the one or more connection ports that is positioned superior to the patient's otobasion superior, and wherein in the second use configuration, the air circuit is connected to a connection port of the one or more connection ports that is positioned inferior to the patient's otobasion superior.

In one example, the one or more positioning and stabilising structures comprises first and second positioning and stabilising structures configured to be interchangeably provided as part of the patient interface, wherein a) the first positioning and stabilising structure is configured for use with the patient interface in the first use configuration and b) the second positioning and stabilising structure is configured for use with the patient interface in the second use configuration.

In this example, the first positioning and stabilising structure comprises at least one gas delivery tube being constructed and arranged to contact at least a region of the patient's head superior to an otobasion superior of the patient's in use, wherein a portion of the gas delivery tube superior to the otobasion superior of the patient's head is provided to the connection port.

In this example, the second positioning and stabilising structure comprises one or more straps, constructed and arranged to contact at least a region of the patient's head superior to an otobasion superior of the patient's head. Further in this example, in the second use configuration, the connection port to which the air circuit is connected is provided to an anterior side of the plenum chamber. In this example, the one or more connection ports may comprise first and second connection ports, wherein the first connection port is provided to the first positioning and stabilising structure, wherein the portion of the gas delivery tube superior to the otobasion superior of the patient's head is provided with the first connection port, and wherein the second connection port is provided to an anterior side of the plenum chamber; and wherein a) when the air circuit is connected to the first connection port in the first use configuration, the second connection port receives a vent structure or a stop; and b) when the air circuit is connected to the second connection port in the second use configuration, the first connection port receives a vent structure or a stop.

In another example, the one or more positioning and stabilising structures comprise a positioning and stabilising structure comprising at least one gas delivery tube being constructed and arranged to contact at least a region of the patient's head superior to an otobasion superior of the patient's head in use, and the one or more connection ports comprise a first connection port provided to a portion of the gas delivery tube superior to the otobasion superior of the patient's head and a second connection port provided to an anterior side of the plenum chamber, wherein the patient interface further comprises one or more vent structures or stops, each vent structure or stop configured to connect to the first and/or second connection port, and wherein, in the first use configuration, the air circuit is connected to the first connection port and one of the vent structures or stops is connected to the second connection port, and, in the second use configuration, the air circuit is connected to the second connection port and one of the vent structures or stops is connected to the first connection port.

In some examples: (a) the first and second connection ports are provided with a closure; (b) the closure is configured to be moveable from a closed condition to an open condition; (c) the closure comprises an opening and at least one closure lid covering at least a portion of the opening when in the closed condition; (d) the closure comprises a ring structure circumscribing the opening; (e) the closure lid is pivotally hinged by an outer edge to the ring structure; (f) the closure lid is slideably mounted to the ring structure, wherein the ring structure is provided with a track along which the closure lid is configured to slide; (g) the closure comprises an opening and at least one closure flap covering at least a portion of the opening when in the closed condition and arranged to be biased from the closed condition to the open condition by an end portion of the air circuit; (h) the closure comprises a ring structure circumscribing the opening; (i) the at least one closure flap is pivotally hinged by an outer edge to the ring structure; (j) the at least one closure flap is pivotally hinged to a strut spanning the opening of the ring; (k) the at least one closure flap spans the opening or ring structure and is provided with a central aperture which increases in size as the closure is biased from the closed condition to the open condition by the end portion of the air circuit; (l) the end portion of the air circuit includes an activation mechanism arranged to act against the closure; (m) the closure includes a vent; the vent is in the form of one or more apertures provided to the closure lid or closure flap; (n) the closure comprises two or more closure flaps, and wherein the vent is in the form of a slit formed by a distance between adjacent closure flaps; (o) the closure comprises four closure flaps attached to an inside surface of the closure, and wherein the vent is in the form of two intersecting slits formed by a distance between adjacent closure flaps; (p) when in the open condition the closure allows delivery of the flow of air to the entrance of the patient's airways, and wherein, when in the first use configuration, the closure of the first connection port is in an open condition and the closure of the second connection port is in a closed condition, and wherein, when in the second use configuration, the closure of the first connection port is in a closed condition and the closure of the second connection port is in an open condition; (q) the patient interface comprises more than one plenum chamber, wherein each plenum chamber is configured to be interchangeably comprised as part of the patient interface; (r) the patient interface comprises more than one seal-forming structure, wherein each seal-forming structure is configured to be interchangeably comprised as part of the patient interface; and/or (s) the plenum chamber(s) and/or seal-forming structure(s) are configured as one or more of: a nasal mask, nasal cushion, nasal pillows or a full-face mask.

In yet another example, the one or more positioning and stabilising structures comprises first and second positioning and stabilising structures, wherein a) the first positioning and stabilising structure comprises at least one gas delivery tube, and b) the second positioning and stabilising structure includes one or more straps, and the one or more connection ports comprise a connection port provided to the first positioning and stabilising structure, where, in the first use configuration, the first positioning and stabilising structure is donned to contact at least a region of the patient's head superior to an otobasion superior of the patient's head and the connection port receives the flow of air from the air circuit, and, in the second use configuration, the second positioning and stabilising structure is donned to contact at least a region of the patient's head superior to an otobasion superior of the patient's head and the connection port receives the flow of air from the air circuit.

In this example, the gas delivery tube has an inferior end configured to be connected to a side of the plenum chamber, wherein the connection between the gas delivery tube and the side of the plenum chamber is configured such that the first positioning and stabilising structure is moveable between a first connection position in the first use configuration and a second connection position in the second use configuration.

In an example, the one or more positioning and stabilising structures comprise a positioning and stabilising structure comprising at least one gas delivery tube being constructed and arranged to contact at least a region of the patient's head superior to an otobasion superior of the patient's head in use, and the one or more connection ports comprise a first connection port provided to a portion of the gas delivery tube superior to the otobasion superior of the patient's head and a second connection port provided to an anterior side of the plenum chamber, wherein the first and second connection ports are provided with a closure, wherein the closure is configured to be moveable from a closed condition to an open condition, wherein, when in the open condition the closure allows delivery of the flow of air to the entrance of the patient's airways, and wherein, when in the first use configuration, the closure of the first connection port is in an open condition and the closure of the second connection port is in a closed condition, and wherein, when in the second use configuration, the closure of the first connection port is in a closed condition and the closure of the second connection port is in an open condition.

It will be understood that a downstream end portion of the air circuit interchangeably connects to the first and second connection ports such that, when in the first use configuration, a downstream end portion of the air circuit is superior to the patient's otobasion superior, and when in the second use configuration, the downstream end portion of the air circuit is inferior to the patient's otobasion superior.

In examples, the patient interface comprises more than one plenum chamber, wherein each plenum chamber is configured to be interchangeably comprised as part of the patient interface.

In examples, the patient interface comprises more than one seal-forming structure, wherein each seal-forming structure is configured to be interchangeably comprised as part of the patient interface.

In examples, the plenum chamber(s) and/or seal-forming structure(s) are configured as one or more of: a nasal mask, nasal cushion, nasal pillows or a full-face mask.

One aspect of the present technology is directed to a patient interface for delivery of a flow of pressurised air from an air circuit to an entrance of a patient's airways, the patient interface comprising:

a plenum chamber;

a seal-forming structure provided to the plenum chamber;

a first positioning and stabilising structure configured to provide a force to hold the seal-forming structure in a therapeutically effective position on a patient's head in use, wherein the first positioning and stabilising structure comprises at least one gas delivery tube being constructed and arranged to contact, in a first use configuration, at least a region of the patient's head superior to an otobasion superior of the patient's head, wherein a portion of the gas delivery tube superior to the otobasion superior of the patient's head is provided with a first connection port to receive the flow of air from the air circuit and to deliver the flow of air to the entrance of the patient's airways via the seal-forming structure in the first use configuration; and a second positioning and stabilising structure configured to provide a force to hold the seal-forming structure in a therapeutically effective position on a patient's head in use, wherein, in a second use configuration, the second positioning and stabilising structure is constructed and arranged to contact at least a region of the patient's head superior to an otobasion superior of the patient's head;

a second connection port to receive the flow of air from the air circuit, wherein the second connection port is provided to an anterior side of the plenum chamber, wherein, in the second use configuration, the second connection port receives the flow of air from the air circuit to deliver the flow of air to the seal-forming structure; and a vent structure or stop configured to connect to the second connection port in the first use configuration.

It will be understood that, the air circuit interchangeably connects to the first and second connection ports such that, when in the first use configuration, a downstream end of the air circuit is superior to the patient's otobasion superior, and when in the second use configuration, the downstream end of the air circuit is inferior to the patient's otobasion superior.

In examples, the patient interface includes a vent structure, wherein the vent structure is provided to: a) the plenum chamber; b) the seal-forming structure; or c) the gas delivery tube.

In examples, the patient interface comprises more than one plenum chamber, wherein each plenum chamber is configured to be interchangeably comprised as part of the patient interface.

In examples, the patient interface comprises more than one seal-forming structure, wherein each seal-forming structure is configured to be interchangeably comprised as part of the patient interface.

In examples, the plenum chamber(s) and/or seal-forming structure(s) are configured as one or more of: a nasal mask, nasal cushion, nasal pillows or a full-face mask.

Another aspect of the present technology is directed to a patient interface for delivery of a flow of pressurised air to an entrance of a patient's airways, the patient interface comprising:

a plenum chamber;

a seal-forming structure provided to the plenum chamber; and a positioning and stabilising structure configured to provide a force to hold the seal-forming structure in a therapeutically effective position on a patient's head in use, wherein the positioning and stabilising structure includes at least one gas delivery tube being constructed and arranged to contact at least a region of the patient's head superior to an otobasion superior of the patient's head, wherein a portion of the gas delivery tube superior to the otobasion superior of the patient's head is provided with a first connection port to, in a first use configuration, receive the flow of air from an air circuit and to deliver the flow of air to the entrance of the patient's airways via the seal-forming structure, wherein an anterior side of the plenum chamber is provided with a second connection port to, in a second use configuration, receive the flow of air from the air circuit and to deliver the flow of air to the entrance of the patient's airways via the seal-forming structure, and wherein the patient interface further comprises one or more vent structures or stops, each vent structure or stop configured to connect to the first and/or second connection port, and wherein, in the first use configuration, the air circuit is connected to the first connection port and one of the vent structures or stops is connected to the second connection port, and, in the second use configuration, the air circuit is connected to the second connection port and one of the vent structures or stops is connected to the first connection port.

It will be understood that, the air circuit interchangeably connects to the first and second connection ports such that, when in the first use configuration, a downstream end of the air circuit is superior to the patient's otobasion superior, and when in the second use configuration, the downstream end of the air circuit is inferior to the patient's otobasion superior.

In examples, the patient interface includes a vent structure, wherein the vent structure is provided to: a) the plenum chamber; b) the seal-forming structure; or c) the gas delivery tube.

In one example the one or more vent structures or stops comprises a vent structure configured to connect to the second connection port in the first use configuration and the first connection port in the second use configuration. In another example the one or more vent structures or stops comprises a stop configured to connect to the second connection port in the first use configuration and the first connection port in the second use configuration.

In examples, the plenum chamber(s) and/or seal-forming structure(s) are configured as one or more of: a nasal mask, nasal cushion, nasal pillows or a full face mask.

Yet another aspect of the present technology is directed to a patient interface for delivery of a flow of pressurised air from an air circuit to an entrance of a patient's airways, the patient interface comprising:

a plenum chamber;

a seal-forming structure provided to the plenum chamber; and a first positioning and stabilising structure configured to provide a force to hold the seal-forming structure in a therapeutically effective position on a patient's head in use, wherein the first positioning and stabilising structure includes at least one gas delivery tube being constructed and arranged to contact, in a first use configuration, at least a region of the patient's head superior to an otobasion superior of the patient's head, wherein a portion of the gas delivery tube superior to the otobasion superior of the patient's head in the first use configuration is provided with a connection port to receive the flow of air from the air circuit and to deliver the flow of air to the entrance of the patient's airways via the seal-forming structure, and wherein the gas delivery tube has an inferior end configured to be connected to a side of the plenum chamber; and a second positioning and stabilising structure configured to provide a force to hold the seal-forming structure in a therapeutically effective position on a patient's head in use, the second positioning and stabilising structure including at least one strap being constructed and arranged to contact, in a second use configuration, at least a region of the patient's head superior to an otobasion superior of the patient's head, wherein the inferior end of the gas delivery tube is connected to the side of the plenum chamber in a manner such that the first positioning and stabilising structure is moveable between the first use configuration and the second use configuration, wherein in the second use configuration, the connection port is inferior to the otobasion superior.

Another aspect of the present technology is directed to a patient interface for delivery of a flow of pressurised air to an entrance of a patient's airways, the patient interface comprising:

a plenum chamber;

a seal-forming structure provided to the plenum chamber; and a positioning and stabilising structure configured to provide a force to hold the seal-forming structure in a therapeutically effective position on a patient's head in use, wherein the positioning and stabilising structure includes at least one gas delivery tube being constructed and arranged to contact at least a region of the patient's head superior to an otobasion superior of the patient's head, wherein a portion of the gas delivery tube superior to the otobasion superior of the patient's head is provided with a first connection port to, in a first use configuration, receive the flow of air from an air circuit and to deliver the flow of air to the entrance of the patient's airways via the seal-forming structure, wherein an anterior side of the plenum chamber is provided with a second connection port to, in a second use configuration, receive the flow of air from the air circuit and to deliver the flow of air to the entrance of the patient's airways via the seal-forming structure, and wherein the first and second connection ports are each configured with a closure, wherein the closure is arranged to be moveable from a closed condition to an open condition, wherein, when in the open condition the closure allows delivery of the flow of air to the entrance of the patient's airways, and wherein, when in the first use configuration, the closure of the first connection port is in an open condition and the closure of the second connection port is in a closed condition, and wherein, when in the second use configuration, the closure of the first connection port is in a closed condition and the closure of the second connection port is in an open condition.

It will be understood that a downstream end portion of the air circuit interchangeably connects to the first and second connection ports such that, when in the first use configuration, the downstream end portion of the air circuit is superior to the patient's otobasion superior, and when in the second use configuration, the downstream end of the air circuit is inferior to the patient's otobasion superior.

In examples, the closure comprises an opening and at least one closure lid covering at least a portion of the opening when in the closed condition. In these examples, the closure further comprises a ring structure circumscribing the opening and the closure lid is a) pivotally hinged by an outer edge to the ring structure; or b) slideably mounted to the closure, wherein the closure is provided with a track along which the closure lid is configured to slide.

In other examples, the closure comprises an opening and at least one closure flap covering at least a portion of the opening when in the closed condition and arranged to be biased from the closed condition to the open condition by the downstream end portion of the air circuit. In these examples, the closure further comprises a ring structure circumscribing the opening and the at least one closure flap is a) pivotally hinged by an outer edge to the ring structure; or b) pivotally hinged to a strut spanning the opening of the ring structure; or c) spans the opening and is provided with a central aperture which increases in size as the closure is biased from the closed condition to the open condition by the downstream end portion of the air circuit.

In a further example, an activation mechanism may be provided at or near the downstream end portion of the air circuit to act upon the closure in response to a connection between the air circuit and the connection port being established. In this example, the activation mechanism may be configured as a protrusion or plurality of protrusions which bear against a surface of the closure to move it from a closed condition to an open condition. In this example, the closure may be temporarily deformable or biased such that it can return to a closed condition once the downstream end portion of the air circuit has been removed.

In examples, the closure also includes a vent. In these examples, the vent is in the form of one or more apertures provided to the closure lid or flap. In other examples, where the closure comprises two or more closure flaps, the vent is in the form of a slit formed by the distance between adjacent closure flaps.

One aspect of the present technology is directed to a patient interface for delivery of a flow of pressurised air to an entrance of a patient's airways, the patient interface comprising:

a plenum chamber;

a seal-forming structure provided to the plenum chamber; and a positioning and stabilising structure configured to provide a force to hold the seal-forming structure in a therapeutically effective position on a patient's head in use, wherein the positioning and stabilising structure includes at least one gas delivery tube being constructed and arranged to contact at least a region of the patient's head superior to an otobasion superior of the patient's head, wherein a portion of the gas delivery tube superior to the otobasion superior of the patient's head is provided with a first connection port to, in a first use configuration, receive the flow of air from an air circuit and to deliver the flow of air to the entrance of the patient's airways via the seal-forming structure, wherein an anterior side of the plenum chamber is provided with a second connection port to, in a second use configuration, receive the flow of air from the air circuit and to deliver the flow of air to the entrance of the patient's airways via the seal-forming structure, and wherein the first and second connection ports are each configured with a closure, wherein the closure is arranged to be moveable from a closed condition to an open condition, wherein, when in the open condition the closure allows delivery of the flow of air to the entrance of the patient's airways, and wherein, when in the first use configuration, the closure of the first connection port is in an open condition and the closure of the second connection port is in a closed condition, and wherein, when in the second use configuration, the closure of the first connection port is in a closed condition and the closure of the second connection port is in an open condition.

It will be understood that the air circuit interchangeably connects to the connection port such that, when in the first use configuration, a downstream end of the air circuit is superior to the patient's otobasion superior and when in the second use configuration, the downstream end of the air circuit is inferior to the patient's otobasion superior.

In examples, the plenum chamber(s) and/or seal-forming structure(s) are configured as one or more of: a nasal mask, nasal cushion, nasal pillows or a full face mask.

Another aspect of one form of the present technology is a patient interface that is moulded or otherwise constructed with a perimeter shape which is complementary to that of an intended wearer.

An aspect of one form of the present technology is a method of manufacturing apparatus.

An aspect of certain forms of the present technology is a medical device that is easy to use, e.g. by a person who does not have medical training, by a person who has limited dexterity, vision or by a person with limited experience in using this type of medical device.

An aspect of one form of the present technology is a patient interface that may be washed in a home of a patient, e.g., in soapy water, without requiring specialised cleaning equipment.

Of course, portions of the aspects may form sub-aspects of the present technology. Also, various ones of the sub-aspects and/or aspects may be combined in various manners and also constitute additional aspects or sub-aspects of the present technology.

Other features of the technology will be apparent from consideration of the information contained in the following detailed description, abstract, drawings and claims.

4 BRIEF DESCRIPTION OF DRAWINGS

The present technology is illustrated by way of example, and not by way of limitation, in the figures of the accompanying drawings, in which like reference numerals refer to similar elements including:

4.1 Respiratory Therapy Systems

FIG. 1A shows a system including a patient 1000 wearing a patient interface 3000, in the form of nasal pillows, receiving a flow or supply of air at positive pressure from an RPT device 4000. Air from the RPT device 4000 is conditioned in a humidifier 5000, and passes along an air circuit 4170 to the patient 1000. A bed partner 1100 is also shown. The patient is sleeping in a supine sleeping position.

FIG. 1B shows a system including a patient 1000 wearing a patient interface 3000, in the form of a nasal mask, receiving a flow or supply of air at positive pressure from an RPT device 4000. Air from the RPT device is humidified in a humidifier 5000, and passes along an air circuit 4170 to the patient 1000.

FIG. 1C shows a system including a patient 1000 wearing a patient interface 3000, in the form of a full-face mask, receiving a flow or supply of air at positive pressure from an RPT device 4000. Air from the RPT device is humidified in a humidifier 5000, and passes along an air circuit 4170 to the patient 1000. The patient is sleeping in a side sleeping position.

4.2 Facial Anatomy

FIG. 2 is a side view of a head with several features of surface anatomy identified including the otobasion superior and otobasion inferior. Also indicated are the directions superior & inferior, and anterior & posterior.

4.3 Patient Interface

5 DETAILED DESCRIPTION OF EXAMPLES OF THE TECHNOLOGY

Before the present technology is described in further detail, it is to be understood that the technology is not limited to the particular examples described herein, which may vary. It is also to be understood that the terminology used in this disclosure is for the purpose of describing only the particular examples discussed herein, and is not intended to be limiting.

The following description is provided in relation to various examples which may share one or more common characteristics and/or features. It is to be understood that one or more features of any one example may be combinable with one or more features of another example or other examples. In addition, any single feature or combination of features in any of the examples may constitute a further example.

5.1 Therapy

In one form, the present technology comprises a method for treating a respiratory disorder comprising applying positive pressure to the entrance of the airways of a patient 1000.

In certain examples of the present technology, a supply of air at positive pressure is provided to the nasal passages of the patient via one or both nares.

In certain examples of the present technology, mouth breathing is limited, restricted or prevented.

5.2 Respiratory Therapy Systems

Figure 1A:
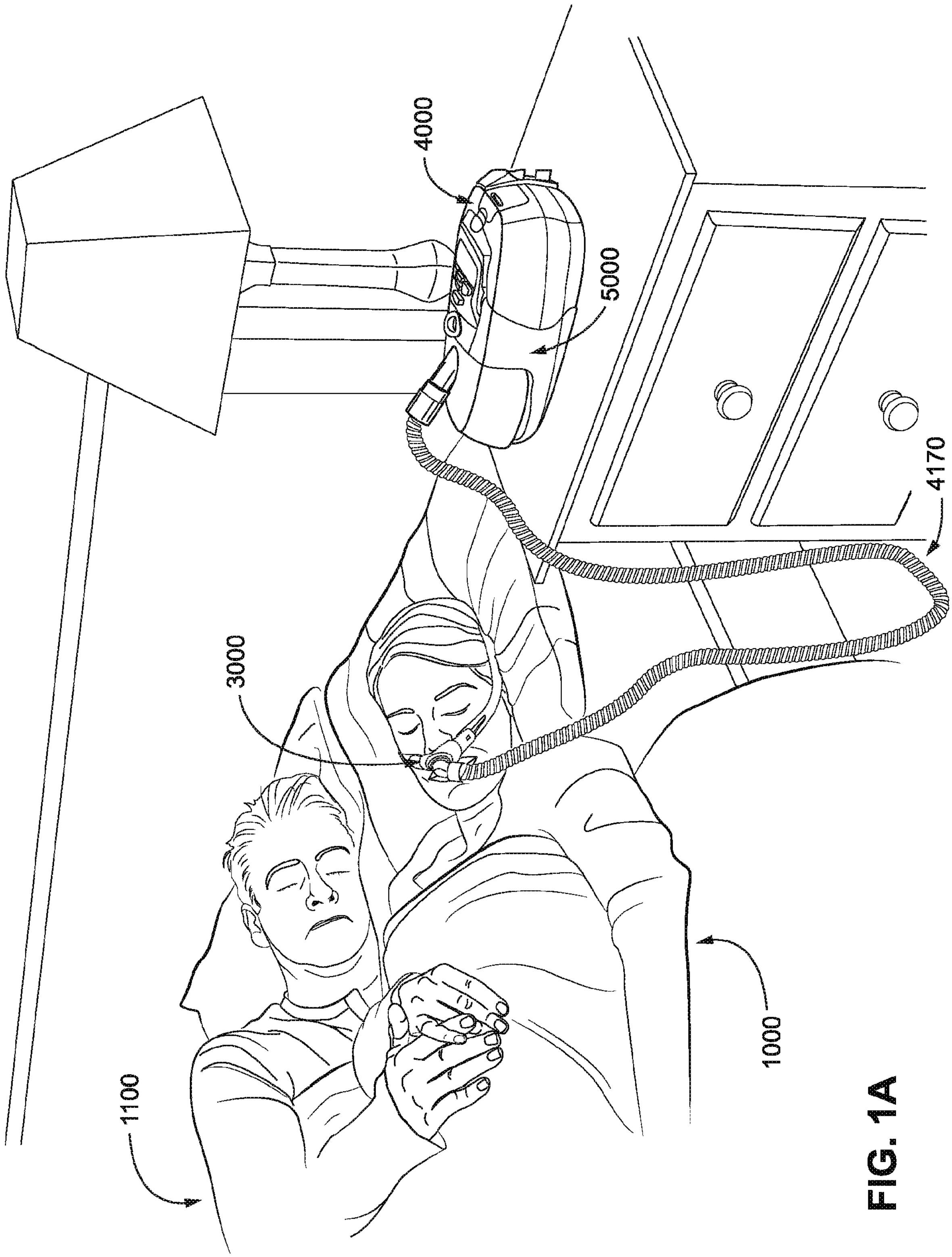
Figure 1B:
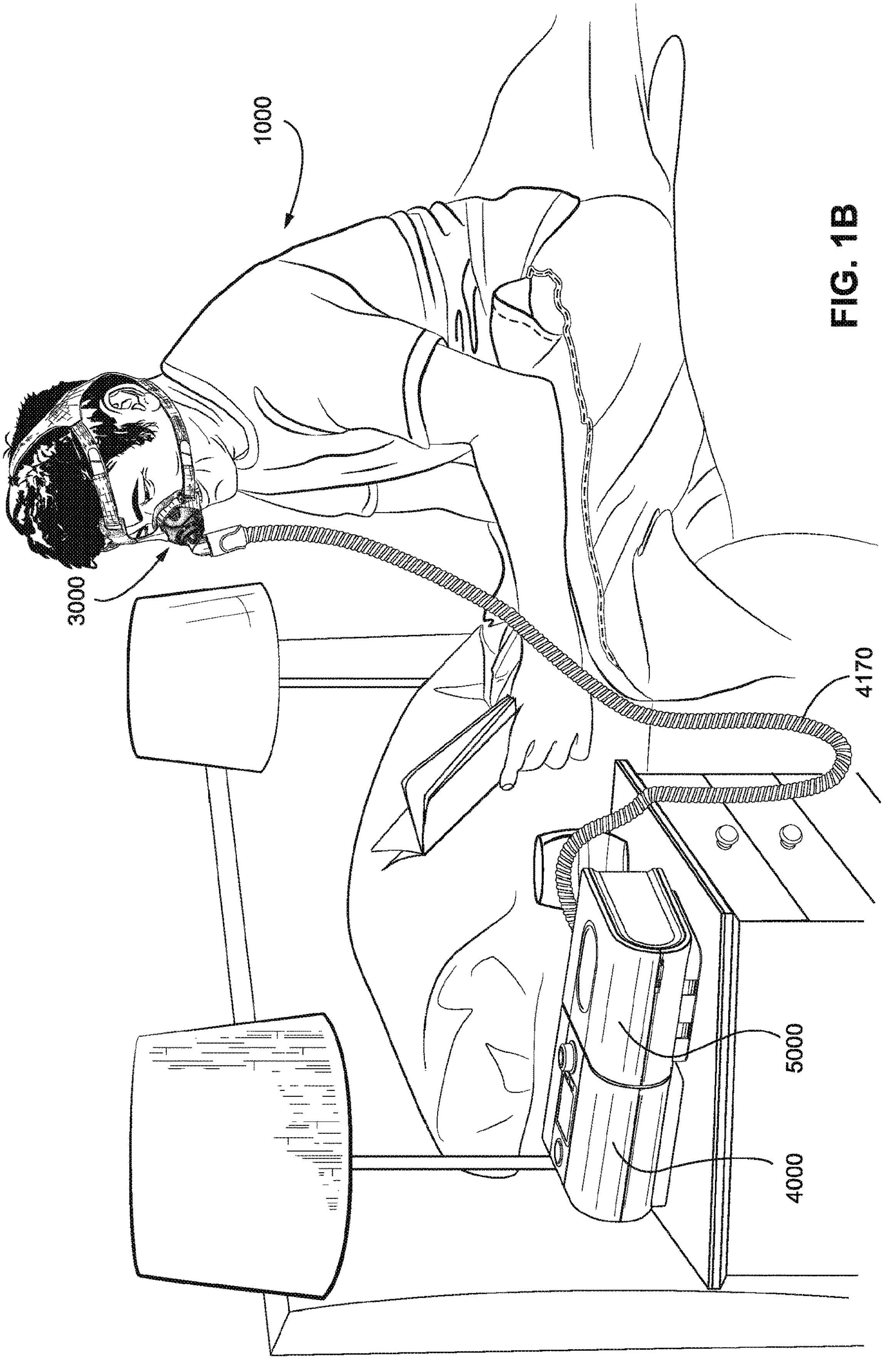
Figure 1C:

In one form, the present technology comprises a respiratory therapy system for treating a respiratory disorder. As shown in FIGS. 1A to 1C, the respiratory therapy system may comprise an RPT device 4000 for supplying a flow of pressurised air to the patient 1000 via an air circuit 4170 and a patient interface 3000.

5.2.1 Air Circuit

The air circuit comprises the conduit that delivers the flow of pressurised air to the patient interface. It is typically a length of tubing of biocompatible plastics material fluidly connected at an upstream end to the RPT device 4000 and to the patient interface 3000 at a downstream end. In some examples, the downstream end portion of the air circuit 4170 is configured as a connector that engages with the patient interface 3000. This engagement may be by way of snap-lock fittings, complementary threads or similar arrangements.

5.2.2 Patient Interface

A non-invasive patient interface 3000 in accordance with one aspect of the present technology comprises the following functional aspects: a seal-forming structure 3100, a plenum chamber 3200, a positioning and stabilising structure 3300, a vent structure 3400, and one form of connection port, either 3600A or 3600B, for connection to the downstream end of the air circuit 4170.

In some forms a functional aspect may be provided by one or more physical components. In some forms, one physical component may provide one or more functional aspects. In use the seal-forming structure 3100 is arranged to surround an entrance to the airways of the patient so as to maintain positive pressure at the entrance(s) to the airways of the patient 1000. The sealed patient interface 3000 is therefore suitable for delivery of positive pressure therapy.

If a patient interface is unable to comfortably deliver a minimum level of positive pressure to the airways, the patient interface may be unsuitable for respiratory pressure therapy.

The patient interface 3000 in accordance with one form of the present technology is constructed and arranged to be able to provide a supply of air at a positive pressure of at least 6 $cmH_2O$ with respect to ambient. In another form of the present technology, the patient interface is constructed and arranged to be able to provide a supply of air at a positive pressure of at least 10 $cmH_2O$ with respect to ambient. In yet another form of the present technology, the patient interface 3000 is constructed and arranged to be able to provide a supply of air at a positive pressure of at least 20 $cmH_2O$ with respect to ambient.

5.2.3 Seal-Forming Structure

In one form of the present technology, the patient interface includes a seal-forming structure 3100 that provides a target seal-forming region and may additionally provide a cushioning function. The target seal-forming region is a region on the seal-forming structure 3100 where sealing may occur. The region where sealing actually occurs—the actual sealing surface—may change within a given treatment session, from day to day, and from patient to patient, depending on a range of factors including for example, where the patient interface was placed on the face, tension in the positioning and stabilising structure and the shape of a patient's face.

In one form the target seal-forming region is located on an outside surface of the seal-forming structure 3100.

In certain forms of the present technology, the seal-forming structure 3100 is constructed from a biocompatible material, e.g. silicone rubber.

A seal-forming structure 3100 in accordance with the present technology may be constructed from a soft, flexible, resilient material such as silicone.

In certain forms of the present technology, a system is provided comprising more than one a seal-forming structure 3100, each being configured to correspond to a different size and/or shape range. For example, the system may comprise one form of a seal-forming structure 3100 suitable for a large sized head, but not a small sized head and another suitable for a small sized head, but not a large sized head.

5.2.3.1 Sealing Mechanisms

In one form, the seal-forming structure includes a sealing flange utilizing a pressure assisted sealing mechanism. In use, the sealing flange can readily respond to a system positive pressure in the interior of the plenum chamber 3200 acting on its underside to urge it into tight sealing engagement with the face. The pressure assisted mechanism may act in conjunction with elastic tension in the positioning and stabilising structure.

In one form, the seal-forming structure 3100 comprises a sealing flange and a support flange. The sealing flange comprises a relatively thin member with a thickness of less than about 1 mm, for example about 0.25 mm to about 0.45 mm, which extends around the perimeter of the plenum chamber 3200. Support flange may be relatively thicker than the sealing flange. The support flange is disposed between the sealing flange and the marginal edge of the plenum chamber 3200, and extends at least part of the way around the perimeter. The support flange is or includes a spring-like element and functions to support the sealing flange from buckling in use.

In one form, the seal-forming structure may comprise a compression sealing portion or a gasket sealing portion. In use the compression sealing portion, or the gasket sealing portion is constructed and arranged to be in compression, e.g. as a result of elastic tension in the positioning and stabilising structure.

In one form, the seal-forming structure comprises a tension portion. In use, the tension portion is held in tension, e.g. by adjacent regions of the sealing flange.

In one form, the seal-forming structure comprises a region having a tacky or adhesive surface.

In certain forms of the present technology, a seal-forming structure may comprise one or more of a pressure-assisted sealing flange, a compression sealing portion, a gasket sealing portion, a tension portion, and a portion having a tacky or adhesive surface.

5.2.4 Plenum Chamber

The patient interface 3000 includes a plenum chamber 3200 that has a perimeter that is shaped to be complementary to the surface contour of the face of an average person in the region where a seal will form in use. In one form of the present technology, the plenum chamber may be part of a full-face mask, ora-nasal, nasal mask, nasal pillows or nasal cushion.

In use, a marginal edge of the plenum chamber 3200 is positioned in close proximity to an adjacent surface of the face. Actual contact with the face is provided by the seal-forming structure 3100. The seal-forming structure 3100 may extend in use about the entire perimeter of the plenum chamber 3200. In some forms, the plenum chamber 3200 and the seal-forming structure 3100 are formed from a single homogeneous piece of material.

The plenum chamber has an anterior side, which should be understood to be the external surface of the plenum chamber facing away from the patient in use. In some forms of the present technology, the plenum chamber may be comprised of two or more components. In one example, the anterior surface may comprise part of a rigid shell to which other portions of the plenum chamber are connected or mounted, either permanently, through the use of appropriate bonding or over-moulding techniques, or temporarily, through the use of complementary or snap lock fasteners.

In some examples, the plenum chamber and/or seal-forming structure may be configured to be removed from the patient interface and replaced with another plenum chamber and/or seal-forming structure, for example ones that differ structurally in some way, for examples ones of different size, type or shape. In this way, the patient may, for example, swap between a plenum chamber and seal-forming structure configured as a nasal mask, a full-face mask, a nasal cushion, and nasal pillows, or between small, medium and large masks of the same type. The plenum chamber and seal-forming structure may form a sub-assembly or module to make such interchanging more convenient for a patient.

The plenum chamber has a posterior side, which should be understood to be the internal surface of the plenum chamber. The posterior side of the plenum chamber has provided to it the seal-forming structure which, in use, receives the nose and/or mouth of the patient.

In certain forms of the present technology, the plenum chamber 3200 does not cover the eyes of the patient in use. In other words, the eyes are outside the pressurised volume defined by the plenum chamber. Such forms tend to be less obtrusive and/or more comfortable for the wearer, which can improve compliance with therapy.

In certain forms of the present technology, the plenum chamber 3200 is constructed from a transparent material, e.g. a transparent polycarbonate. The use of a transparent material can reduce the obtrusiveness of the patient interface and help improve compliance with therapy. The use of a transparent material can aid a clinician to observe how the patient interface is located and functioning.

In certain forms of the present technology, the plenum chamber 3200 is constructed from a translucent material. The use of a translucent material can reduce the obtrusiveness of the patient interface and help improve compliance with therapy.

5.2.5 Positioning and Stabilising Structure

The seal-forming structure 3100 of the patient interface 3000 of the present technology may be held in a sealing position when being worn by the patient through the use of the positioning and stabilising structure 3300. Positioning and stabilising structure 3300 may be referred to as "headgear" since it contacts and engages with the patient's head in order to hold the patient interface 3000 in a sealing position.

In one form the positioning and stabilising structure 3300 provides a retention force at least sufficient to overcome the effect of the positive pressure in the plenum chamber 3200 to lift off the face.

In one form the positioning and stabilising structure 3300 provides a retention force to overcome the effect of the gravitational force on the patient interface 3000.

In one form the positioning and stabilising structure 3300 provides a retention force as a safety margin to overcome the potential effect of disrupting forces on the patient interface 3000, such as from tube drag, or accidental interference with the patient interface.

In one form of the present technology, a positioning and stabilising structure 3300 is provided that is configured in a manner consistent with being worn by a patient while sleeping. In one example the positioning and stabilising structure 3300 has a low profile, or cross-sectional thickness, to reduce the perceived or actual bulk of the apparatus.

In one form of the present technology, a positioning and stabilising structure 3300 is provided that is configured so as not to be too large and bulky to prevent the patient from lying in a supine sleeping position with a back region of the patient's head on a pillow.

In one form of the present technology, a positioning and stabilising structure 3300 is provided that is configured so as not to be too large and bulky to prevent the patient from lying in a side sleeping position with a side region of the patient's head on a pillow.

In one form of the present technology, a positioning and stabilising structure 3300 is provided with a decoupling portion located between an anterior portion of the positioning and stabilising structure 3300, and a posterior portion of the positioning and stabilising structure 3300. The decoupling portion does not resist compression and may be, e.g. a flexible or floppy strap. The decoupling portion is constructed and arranged so that when the patient lies with their head on a pillow, the presence of the decoupling portion prevents a force on the posterior portion from being transmitted along the positioning and stabilising structure 3300 and disrupting the seal.

5.2.5.1 Headgear Strap(s)

Figure 3A:
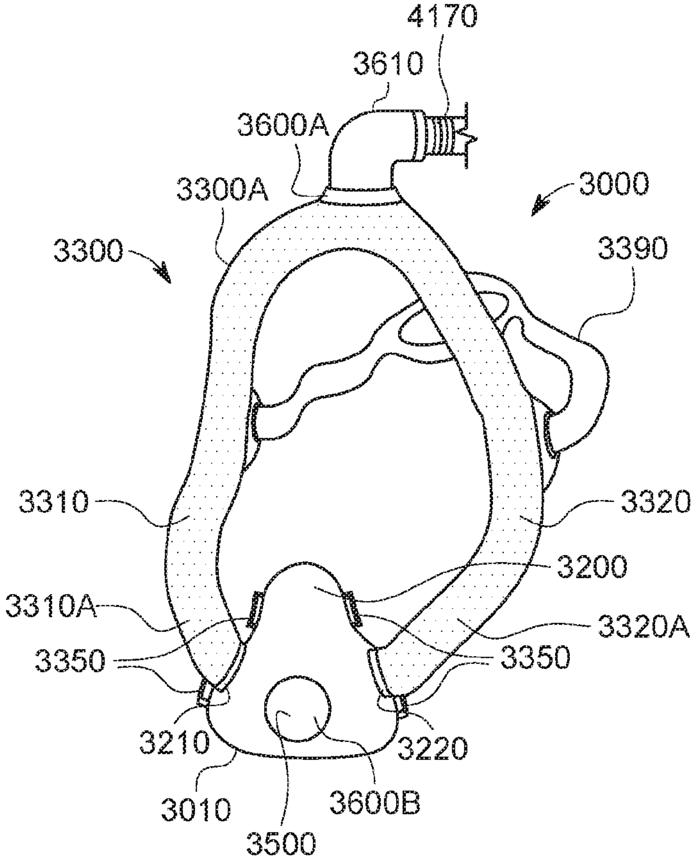
FIG. 3A shows a patient interface in the form of a full-face mask in a first use configuration in accordance with one form of the present technology.
Figure 3B:
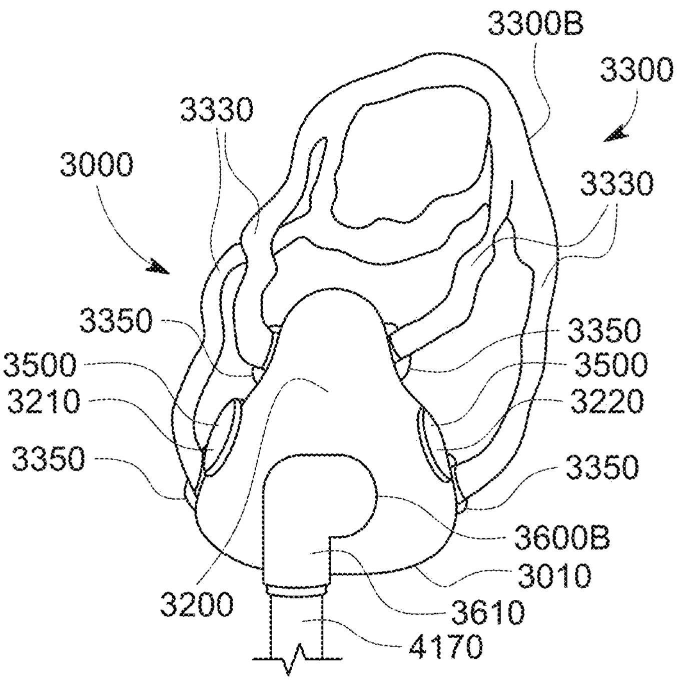
FIG. 3B shows the patient interface of FIG. 3A in a second use configuration in accordance with one form of the present technology.

In one form of the present technology, the positioning and stabilising structure 3300 is in the form of a headstrap arrangement 3300B, as shown in FIG. 3B. The headstrap arrangement 3300B comprises a strap, or plurality of straps 3330, arranged to form a cup for the rear of the patient's head. Collectively, these straps serve to hold the patient interface in place on the face of the patient.

The strap(s) 3330 may be constructed from a laminate of a fabric patient-contacting layer, a foam inner layer and a fabric outer layer. In one form, the foam is porous to allow moisture, (e.g., sweat), to pass through the strap(s) 3330. The strap(s) 3330 may be breathable to allow moisture vapour to be transmitted through the strap. In one form, the fabric outer layer comprises loop material to engage with a hook material portion.

In certain forms of the present technology, the strap(s) 3330 of the positioning and stabilising structure 3300 are configured to be extensible, e.g. resiliently extensible. For example the strap may be configured in use to be in tension, and to direct a force to draw a seal-forming structure into sealing contact with a portion of a patient's face. In an example the strap may be configured as a tie.

In certain forms of the present technology, the strap(s) 3330 of the positioning and stabilising structure 3300 is comprised to be bendable and e.g. non-rigid. An advantage of this aspect is that the strap is more comfortable for a patient to lie upon while the patient is sleeping. The strap(s) 3330 is sufficiently flexible to pass around the back of the patient's head and lie comfortably against the patient's head, even when under tension in use.

In certain examples of the present technology, the positioning and stabilising structures 3300 are configured to receive the strap 3330 at the locations superior to and proximate the patient's ears. If the strap 3330 connects to the positioning and stabilising structures too high with respect to the patient's head, the strap 3330 may have a tendency to ride up the back of the patient's head. Additionally, the strap 3330 could form too large of an angle with respect to the superior portions of the positioning and stabilising structure, resulting in the necessity for the patient to tighten the strap 3330 excessively, which could result in both excessive tension in the positioning and stabilising structure 3300 and make the strap 3330 more likely to ride up the back of the patient's head. Accordingly, it is advantageous for the connection between the strap 3330 and the positioning and stabilising structures to be provided as low as possible but spaced from the top of the patient's ear sufficiently that upon tightening of the strap 3330, the positioning and stabilising structures are not pulled into contact with the patient's ears as this may cause discomfort.

In certain forms of the present technology, a system is provided comprising more than one positioning and stabilizing structure 3300 (e.g. headstrap arrangement 3300B), each being configured to provide a retaining force to correspond to a different size and/or shape range. For example, the system may comprise one form of positioning and stabilizing structure suitable for a large sized head, but not a small sized head, and another, suitable for a small sized head, but not a large sized head.

5.2.5.2 Gas Delivery Tube(s)

Figure 2:
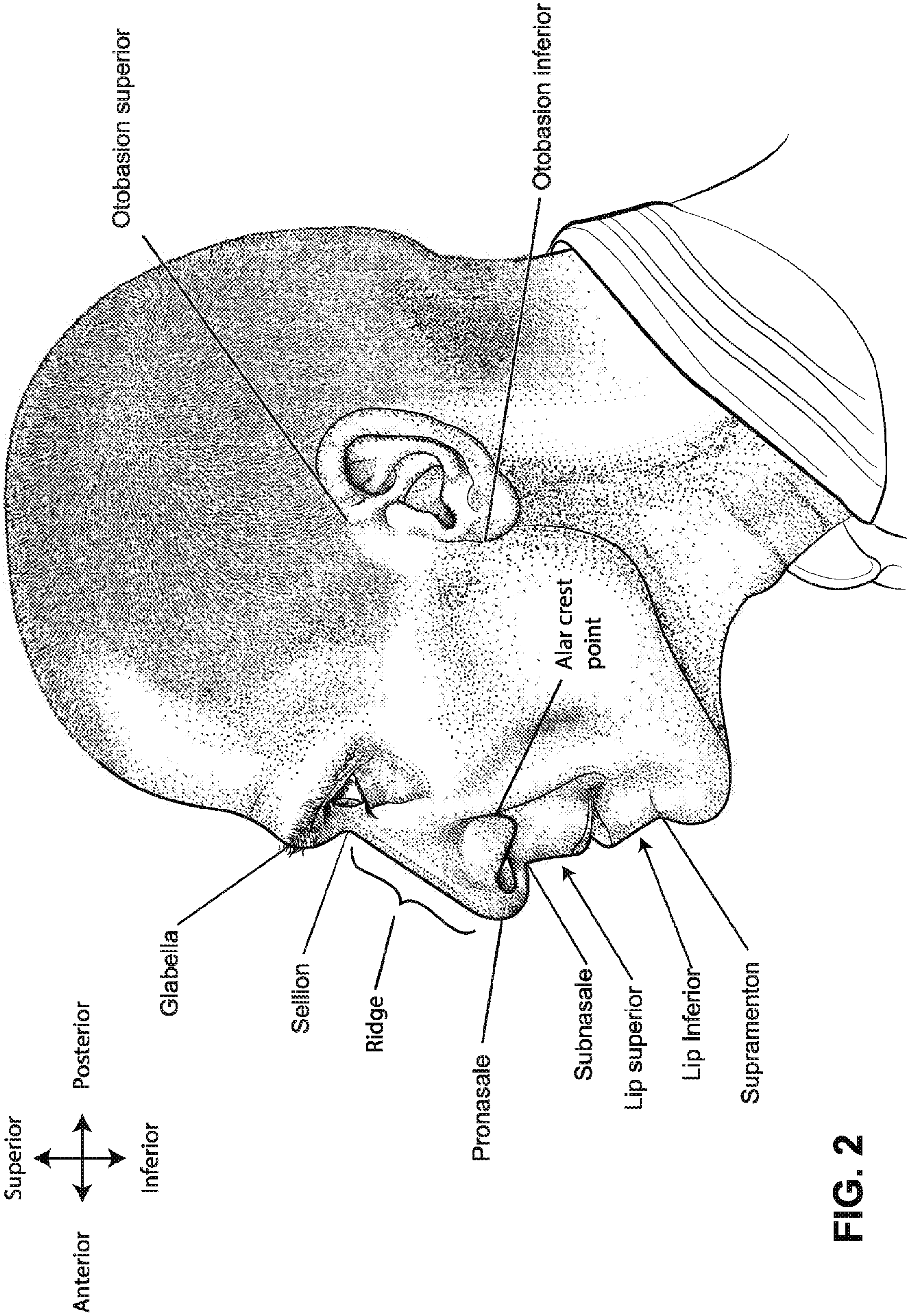
Figure 4A:
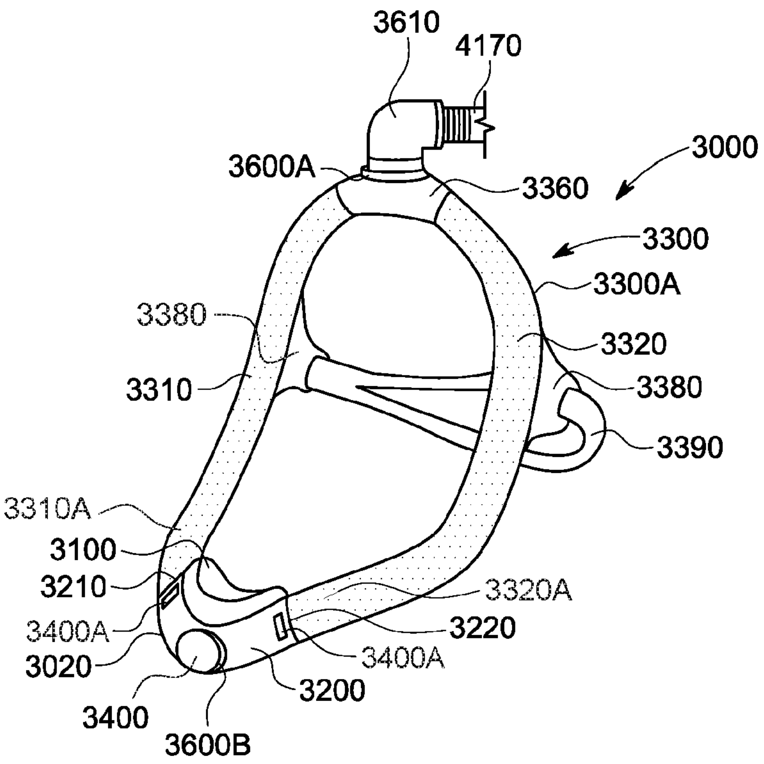
FIG. 4A shows a patient interface in the form of a nasal cushion in a first use configuration in accordance with one form of the present technology.

In some forms of the present technology, for example that of FIGS. 3A and 4A, the positioning and stabilising structure 3300 comprises one or more conduits in the form of gas delivery tubes 3310, 3320 that deliver pressurised air received from the air circuit 4170 from the RPT device to the patient's airways, for example through the plenum chamber 3200 and seal-forming structure (not visible in FIG. 3A). In these forms, the positioning and stabilising structure 3300 may be referred to as conduit headgear 3300A and, as well as delivering pressurised air to the airways, serves to position and stabilise the seal-forming structure 3100 of the patient interface to the appropriate part of the patient's face (the terms tube and conduit should be understood to be interchangeable). In these forms, the conduit headgear contacts at least a region of the patient's head superior to an otobasion superior of the patient's head. As seen in FIG. 2, the otobasion superior is the point on the side of the patient's head that gives rise to the upper portion of the ears.

In one example, the tubes 3310, 3320 may be substantially cylindrical. However, in other examples, the tubes may be formed with a variety of cross-sectional shapes. For example, a substantially D-shaped cross-sectional profile may be used; the flat side of this profile may contact the patient's face when being worn and may be more comfortable than a semi-circular profile.

In some forms of the present technology, the conduit headgear comprises a pair of tubes 3310, 3320 that deliver pressurised air from the downstream end of the air circuit to the seal-forming structure. As an example, in FIG. 4A the tubes 3310, 3320 are joined at their superior ends to a crown connector 3360 that bears a connection port 3600A, to fluidly engage with the downstream end of the air circuit and forms an integral part of the positioning and stabilising structure of the patient interface. At their inferior ends, the tubes are joined to the patient interface 3000 via air entry ports 3210, 3220. The tubes may be disconnected, for example for cleaning or storage.

In some forms of the present technology, as shown in FIG. 4, the conduit headgear 3300A comprises left and right tubes 3310, 3320, which at their inferior ends fluidly engage or otherwise connect to the patient interface 3000, which in this form is a full-face mask 3010, in order to deliver the pressurised air to the seal-forming structure. A connection port 3600A to engage with the downstream end of the air circuit 4170 is provided to the superior portion of the conduit headgear 3300A, where the two arms of the tubes 3310, 3320 meet. At their inferior ends, the arms are joined to the patient interface 3000 via air entry ports near ends of the tubes 3210, 3220. In this example, the conduit headgear is substantially a unitary structure.

In the examples illustrated in FIGS. 3A and 4A, the connection port 3600A is generally located at the crown of the patient when the conduit headgear 3300A is being worn. However, it should be appreciated that the connection port 3600A may be provided to a different location, subject to the shape of the conduit headgear. For example, rather than meeting across the crown of the patient's head, the tubes 3310, 3320 may be arranged to meet further back to the posterior of the patient's head. This would place the connection port proximate a part of the posterior of the patient's head, rather than the crown. Alternatively, the connection port 3600A may be provided elsewhere, for example to one of the two tubes 3310, 3320 rather than where they meet.

In certain examples of the present technology, the conduit headgear 3300A is formed from a suitably sprung material that provides sufficient stabilising forces that correctly locates the patient interface in a sealing arrangement on the patient's head. In certain other examples, the positioning and stabilising structure comprises a mechanism for connecting a headgear strap 3390 or other stabilising component to the headgear tubes. The headgear strap may supplement the stabilising forces provided by the conduit headgear and help correctly locate the patient interface in a sealing arrangement on the patient's head.

In these examples, the headgear strap may be connected directly or indirectly to the headgear tubes 3310, 3320. In the case of the patient interface shown in FIGS. 4A and 4B, for example, a tab 3380, configured to connect to the back strap 3390, projects away from the tubes 3310, 3320 in a generally posterior direction. The tabs 3380 have slits in them to receive the ends of the strap 3390.

The back strap 3390 may be secured to itself after passing through the slits in the tabs 3380, for example, with hook-and-loop fastening material. The back strap 3390 therefore is able to be adjusted to fit around different head sizes. In some forms of the technology, more than one tab may be provided to the tubes 3310, 3320 to provide the patient a range of alternative placement options for the back strap 3390. This may be helpful for ensuring appropriate application of sealing forces to the face.

The tubes 3310, 3320 of the conduit headgear 3300A may be formed from textile, spacer fabric and/or foam materials, in some examples. Portions of the tubes 3310, 3320 that contact the patient may be formed with textiles or fabrics for greater patient comfort. In some examples, the tubes may be formed of a semi-rigid material such as an elastomeric material, e.g. silicone. In these examples, the tubes may comprise thin sleeves of fabric or textiles wrapped around them. The sleeves may be more comfortable against the patient's face than the tubes without any covering.

As shown in FIGS. 3A and 4A, in some examples, the tubes 3310, 3320 of the conduit headgear 3300A may have a natural, preformed shape that conforms to the general shape of the patient's head. In some examples, the tubes 3310, 3320 may have at least some ability to deform if a force is applied to the tubes or conform to a patient's head. For example, the tubes may be generally arcuate or curved in a shape approximating the contours of a patient's head between the top of the head and the nasal or oral region.

Since air can be contained and passed through the tubes 3310, 3320 of the conduit headgear 3300A in order to deliver pressurised air from the air circuit 4170 to the patient's airways, the conduit headgear may be described as being inflatable. It will be understood that an inflatable conduit headgear does not require all its components to be inflatable. For example, when the positioning and stabilising structure comprises the headgear tubes 3310, 3320 and back strap 3390, the headgear tubes are inflatable and the back strap is not inflatable.

5.2.6 Vent Structure

Figure 5A:
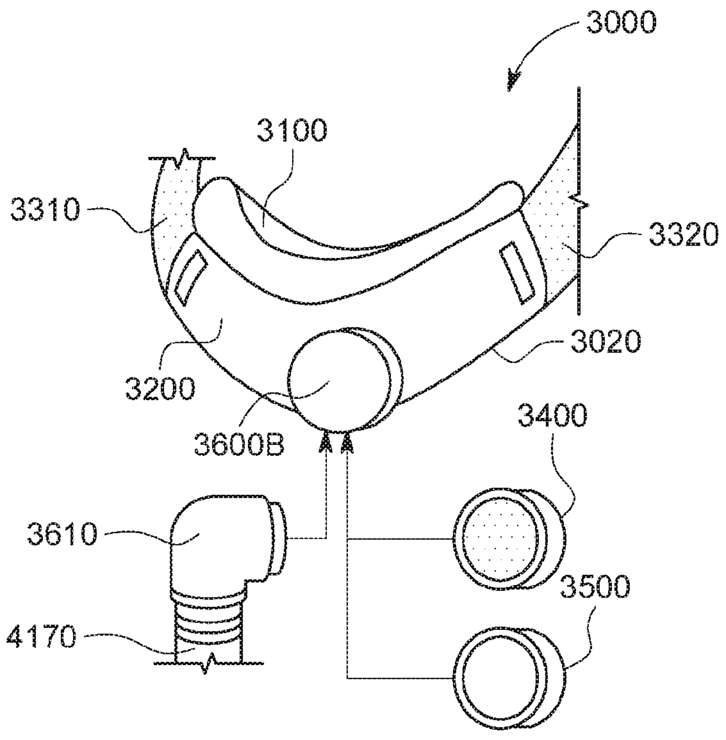
FIG. 5A shows a close up view of the nasal cushion of the patient interface of FIGS. 4A and 4B.

In one form, the patient interface 3000 includes a vent structure 3400 constructed and arranged to allow for the washout of exhaled gases, e.g. carbon dioxide. An example is shown in FIG. 5A, in which the patient interface is in the form of a nasal cushion 3020 (see FIG. 4A and plug structure 3500 in FIG. 3A which may be replaced with a vent structure 3400).

In certain forms the vent structure 3400 is configured to allow a continuous vent flow from an interior of the plenum chamber 3200 to ambient whilst the pressure within the plenum chamber is positive with respect to ambient. The vent structure 3400 is configured such that the vent flow rate has a magnitude sufficient to reduce rebreathing of exhaled $CO_2$ by the patient while maintaining the therapeutic pressure in the plenum chamber in use.

One form of the vent structure 3400 in accordance with the present technology comprises a plurality of holes, for example, about 20 to about 80 holes, or about 40 to about 60 holes, or about 45 to about 55 holes.

In one form of the technology the vent structure 3400 may be configured to be an integral part of the plenum chamber and/or the seal-forming structure. In a further form, the vent structure may be an integral part of the connection port 3600A, 3600B. In yet another form, the vent structure may be an integral part of the positioning and stabilising structure. In other forms of the technology the vent structure 3400 may be a separate component to the plenum chamber, seal-forming structure, connection port and/or positioning and stabilising structure, but may be provided to one of those components. The vent structure may be detachable for cleaning and replacing. In some forms of the present technology, the patient interface may be provided with more than one vent structure.

In one form of the technology the vent structure 3400 is formed from rigid medical grade plastics material. In alternative forms, the vent structure is formed from a soft woven mesh. In these forms, the mesh may be bounded by a rigid or semi-rigid frame to confer some structural integrity to the vent structure. In other forms, it may be formed as a moulding from a rigid plastics material.

As shown in FIG. 5A the vent structure 3400 may be configured to connect to connection port 3600B in plenum chamber 3200. For example, the vent structure 3400 may be generally circular in plan view, or may comprise a generally circular connector for connecting to the connection port 3600B.

Figure 4B:
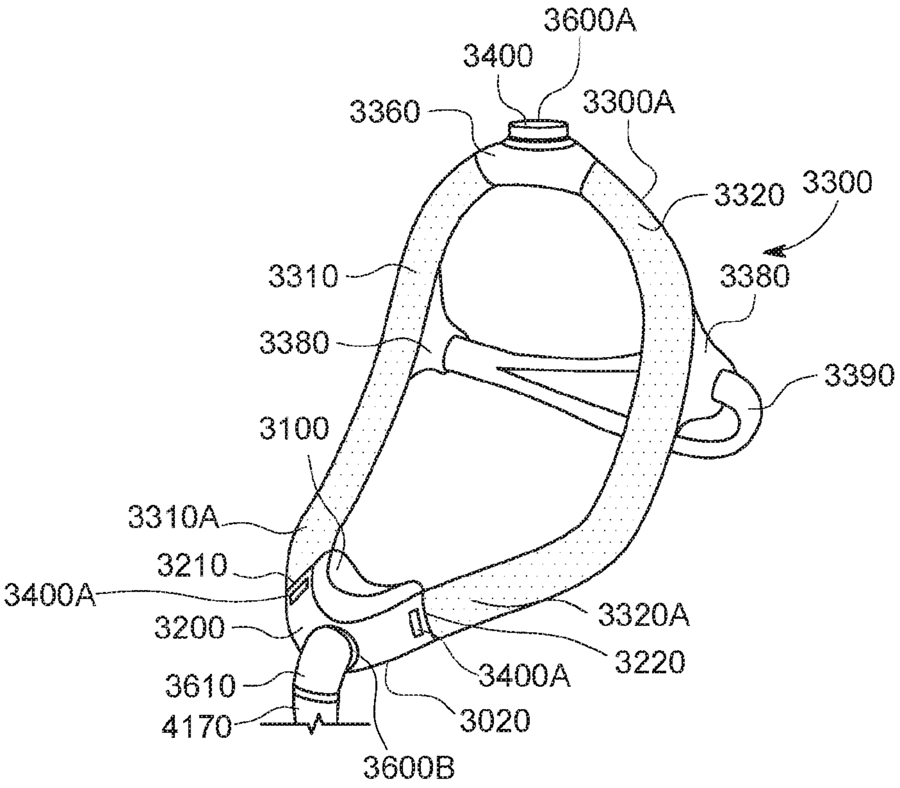
FIG. 4B shows the patient interface of FIG. 4A in a second use configuration in accordance with one form of the present technology.

In one form, one or more additional vent structure 3400A may be provided in the nasal cushion 3020 (see FIGS. 4A and 4B) and/or full face mask 3010. As shown in FIG. 4A the vent structure 3400 and/or 3400A may be configured as part of the plenum chamber 3200. For example, the vent structure 3400A may be a slot or circular in plan view. Alternatively, or in addition to a vent structure in the plenum chamber, the vent structure may be configured as part of the crown connection 3360 of the conduit headgear 3300A as shown in FIG. 4B.

5.2.7 Connection Port

The connection ports 3600A, 3600B allow for connection of the patient interface 3000 to the downstream end portion of the air circuit 4170.

In some examples, such as that shown in FIGS. 3A and 4A, the connection port 3600A, 3600B may comprise an elbow 3610 received in a fluid connection opening of the patient interface 3000. The elbow may be received in a ring in the fluid connection opening and may be configured to swivel within the ring. The fluid connection opening may be also considered a connection port itself.

When the present technology is in use, the location of the connection port 3600A, 3600B, and therefore the location at which the downstream end portion of the air circuit 4170 connects to the patient interface 3000, depends on whether the patient has selected to wear the patient interface in a first use configuration or a second use configuration.

5.2.8 Closure

In one form, the connection ports 3600A, 3600B of the patient interface 3000 and conduit headgear 3300A comprise a closure 3786. The closure is arranged to be moveable between a closed condition, where the connection port is substantially sealed, and an open condition, where pressurised air from the air circuit is able to flow into the connection port. The closure allows the patient to seal or substantially close off the connection port when the air circuit is not connected. The closure may be a separate component, inserted by the patient as required, or formed integrally as part of the connection ports.

In one form of the technology the closure 3786 is formed from rigid medical grade plastics material. In alternative forms, the closure is formed from a softer, semi-rigid material such as silicone or the like. In these forms, the closure may be bounded by a rigid or semi-rigid frame or ring to confer some structural integrity to the closure.

In some examples, the closure 3786 may be constructed and arranged to allow for the washout of exhaled gases, e.g. carbon dioxide. Non-limiting examples of closures for use in these forms of technology are shown in FIGS. 11 to 15.

5.2.9 First Use Configuration/Second Use Configuration

In the present technology, the patient is able to select between a first use configuration and a second use configuration when wearing the patient interface.

The first use configuration should be understood to be an arrangement where, when the patient interface 3000 is being worn with a positioning and stabilising structure 3300 in the form of conduit headgear 3300A, the air circuit 4170 engages with the patient interface at a point superior to the patient's otobasion superior, i.e. the connection port is superior to the patient's otobasion superior. In this configuration, examples of which are shown in FIGS. 3A and 4A, the connection port 3600A is provided to, or configured as part of, the conduit headgear.

This first use configuration places the connection port 3600A and downstream end of the air circuit 4170 generally away from the patient's face. Instead, the downstream end of the air circuit is located proximate the superior side of the patient's head before the remainder of the air circuit extends or falls away down the sides or back of the patient. An informal term for this configuration may be "tube up".

Figure 6:
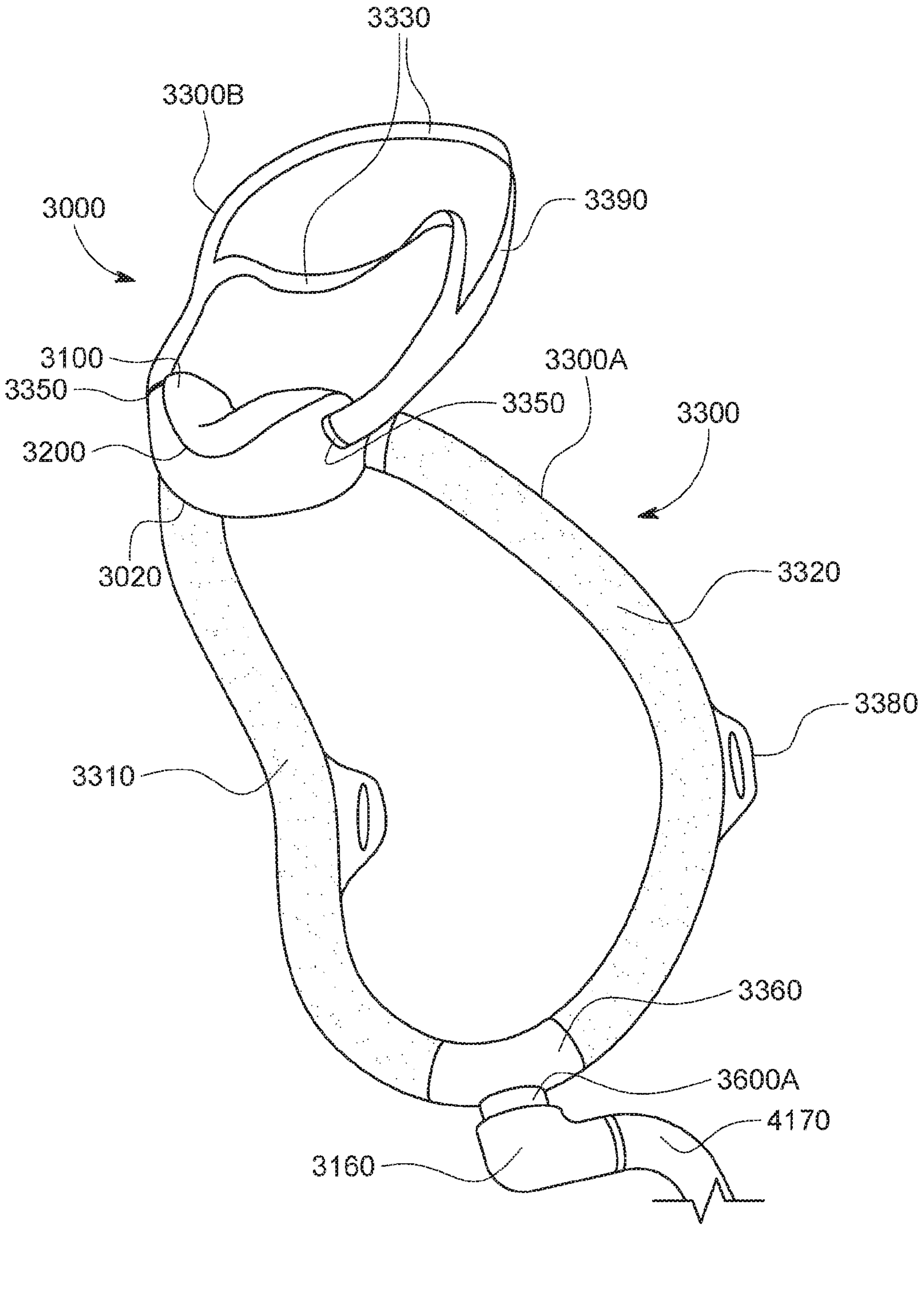
FIG. 6 shows the patient interface of FIG. 4A in an alternative second use configuration in accordance with another form of the present technology.

The second use configuration should be understood to be an arrangement where, when the patient interface 3000 is being worn, the downstream end of the air circuit 4170 engages with the patient interface 3000 at a point inferior to the patient's otobasion superior, i.e. the connection port 3600A is inferior to the patient's otobasion superior. Examples of a patient interface 3000 in the second use configuration are shown in FIGS. 3B, 4B, and 6.

In this second use configuration, the connection port 3600B may be provided to, or configured as part of, the anterior side of the plenum chamber 3200 as shown in FIGS. 3B and 4B. In an alternative example of the second use configuration, shown in FIG. 6, the connection port 3600A may be provided to, or configured as part of, the positioning and stabilising structure 3300 in the form of conduit headgear 3300A. In this alternative example, the conduit headgear 3300A may have been inverted or otherwise rotated away from the first use configuration (where the conduit headgear 3300A contacts at least a region of the patient's head superior to the otobasion superior) to the second use configuration, where the conduit headgear 3300A does not contact the head superior to the otabasion superior. In this alternative example, a second positioning and stabilising structure 3300, for example comprising a plurality of headstraps in a headstrap arrangement 3300B, may be required to ensure the seal-forming structure 3100 is held in place.

In these examples, the second use configuration places the connection port (3600A when part of the conduit headgear, 3600B when part of the plenum chamber) and downstream end of the air circuit 4170 proximate the patient's face or neck. The downstream end of the air circuit is located anterior or inferior to the patient's head, in front of the face or around the chin or neck, before the remainder of the air circuit extends or falls away. An informal term for this configuration may be "tube down".

Patient interfaces in which the connection port is not positioned in front of the patient's face may be advantageous for patients who find an air circuit connecting to a patient interface in front of the face to be unsightly and/or obtrusive. For example, an air circuit connecting to a patient interface in front of the face may be prone to being tangled up in bedclothes or bed linen, particularly if the air circuit extends inferiorly from the patient interface in use. Forms of the technology with a patient interface with a connection port positioned proximate the top of the patient's head in use may make it easier or more comfortable for a patient to lie or sleep in one or more of the following positions: in a side or lateral position; in a supine position (i.e. on their back, facing generally upwards); and in a prone position (i.e. on their front, facing generally downwards). Moreover, connecting a conduit to the front of a patient interface may exacerbate a problem known as tube drag, wherein the conduit may provide an undesired drag force upon the patient interface thereby causing dislodgement of the patient interface away from the face while the patient is sleeping and jeopardising therapy.

Conversely, patient interfaces in which the connection port is positioned in front of the patient's face may be advantageous for some patients, particularly those who do not mind the presence of the air circuit in their sightline and are used to patient interfaces of this type. Some patients may wear the patient interface while awake and when their upper body is generally upright. The presence of the air circuit to the front of their body may be less obtrusive and/or more easily managed.

The present technology is directed towards a patient interface (e.g., a modular patient interface) that allows the patient to select between the first use and second use configurations, i.e. between "tube up" and "tube down" configurations. In some instances, there may be a trade-off between these tube up and tube down configurations.

For example, a tube up configuration when wearing conduit headgear may provide added freedom of movement and less obtrusiveness. It may afford the patient more freedom of choice by avoiding the need for having an air circuit connecting to the front of the patient. This may allow the patient to move more freely or face bed partners easily during therapy. However, a tube up configuration be not as stable when holding the patient interface in sealing contact with the face of the patient as there may be relatively more restrictions in designing conduit headgear that functions dually as both a headgear and a tube that delivers pressurised air, when compared to the design of headgear straps. In the instance where conduit headgear is less stable, it may be provided with a patient interface with a more robust seal forming structure to compensate for a reduction in system stability. In this case, the seal forming structure may be slightly more obtrusive to effect a more robust seal, when compared to a relatively less robust seal forming structure.

During the course of therapy, a patient may choose to alternate between a tube up or tube down configuration depending on their choice between the added freedom of movement and less obtrusiveness that conduit headgear provides versus the added stability of a headgear having straps and buckles. Other benefits include the ability to easily switch between the two configurations. For example, the patient may try the first, "tube up" configuration initially as it provides more freedom and only switch out the conduit headgear for conventional headgear straps if there is inadequate seal formation. Another benefit of a modular patient interface system where the connection ports for the air circuit are either in the patient interface or up the top of the conduit headgear may be a reduction in stock keeping units and therefore less cost to manufacture and reduced choices between systems.

In certain forms of the present technology, the patient interface 3000 may be provided to the patient as a therapy system comprising a plurality of components, to be assembled, connected to each other and interchanged according to personal preference. The patient selects the desired patient interface 3000 and the positioning and stabilising structure 3300 depending on their preference for a "tube up" or a "tube down" use configuration. In these forms, the therapy system may include at least: a patient interface 3000, comprising one or more of the following mask types: full face 3010, nasal mask, and nasal cushion 3020; and positioning and stabilising structure 3300, compromising conduit headgear 3300A and optionally a headstrap arrangement 3300B.

In certain forms of the present technology, the therapy system may include, in addition to the components mentioned above, one or more of the following: connection port 3600; vent structure 3400; plug structure 3500; and adaptors/connectors to facilitate the engagement of respective components to assemble a complete therapy system according to the patient's personal preference.

In some forms of the present technology, additional vents may be provided. In one example, if present, the conduit headgear 3300A may include a series of small openings which serve as vents. In another example, the seal forming structure 3100 may include a series of small openings which serve as vents.

The present technology shall now be described in respect of certain, non-limiting examples.

5.2.9.1 First Example

One example of the present technology is shown in FIG. 3A, with the patient interface 3000 in the first use configuration.

The patient interface includes a plenum chamber and seal-forming structure in the form of a full-face mask 3010 that, when worn by the patient, covers and forms a seal around the nose and mouth, and a positioning and stabilising structure 3300 in the form of conduit headgear 3300A, having left and right tubes 3310, 3320. The two tubes are fluidly connected at their upper ends to each other and to a connection port 3600.

The connection port 3600A is provided in use with an elbow 3610 which receives the downstream end of the air circuit 4170. When the conduit headgear is worn by the patient, the connection port is located superior to the patient's otobasion superior (refer to FIG. 2).

In this example of the present technology, the sides of the plenum chamber 3200 of the full-face mask 3010 are configured with left and right air entry ports 3210, 3220. The left and right air entry ports 3210, 3220 are configured to be in fluid communication with the inferior ends 3310A, 3320A of the tubes of the conduit headgear 3300A. This allows delivery of pressurised air from the air circuit 4170 to the seal-forming structure (not visible in FIG. 3A) of the patient interface 3000 in the first use configuration.

The air entry ports 3210, 3220 and portions of the tubes 3310A, 3320A that engage with same are configured with appropriate attachment mechanisms, for example in the form of complementary male and female fittings, such as interlocking grooves and pegs.

Figure 7:
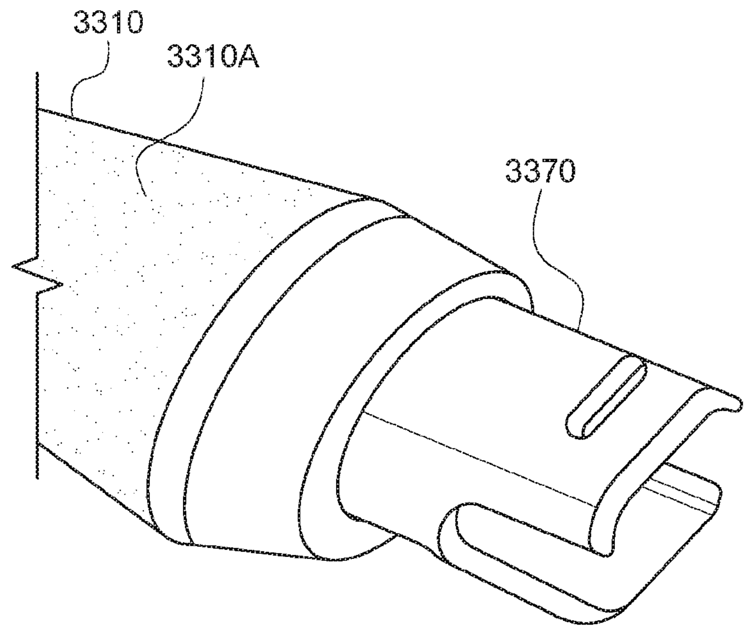
FIG. 7 shows a rigid connector of a tube of a conduit headgear in accordance with one form of the present technology.

One example of the attachment mechanism used to connect the tubes to the air entry ports is shown in respect of the left tube 3310 in FIG. 7. The inferior end 3310A is provided with a rigid connector 3370 made, for example, from polypropylene, polycarbonate, nylon or the like. This rigid connector engages in a sealing arrangement with the air entry port 3210. Alternatively, the attachment mechanisms used to connect the left and right tubes to the air entry ports may be configured as snap-lock fittings, screw threads or the like.

In a hard-to-hard type engagement between the tubes 3310, 3320 and the air entry ports 3210, 3220 of the patient interface 3000, a pressure activated seal such as a peripheral sealing flange may be used. When pressurised gas is supplied through the tubes 3310, 3320 the sealing flange is urged against the join between the tubes and the inner circumferential surface of air entry ports of the plenum chamber to enhance the seal between them. If the air entry ports are soft and a rigid connector is provided to the tube the pressure activated seal as described earlier may also be used to ensure the connection is air-tight, although it may also not be necessary.

The anterior side of the plenum chamber of the full-face mask 3010 is also provided with a connection port 3600B. In a first use configuration of the patient interface as shown in FIG. 3A, this connection port is sealed off with a plug structure 3500, or a vent structure 3400 (an example 3400 is shown in FIG. 5A). The use of a vent structure allows exhaled air to be vented to the exterior of the patient interface.

The vent structure 3400 may be configured as a vent module to be inserted or otherwise engaged into an appropriately configured opening, such as the connection port 3600B in the patient interface 3000. In this form, the vent structure may include flanges or similar structures, which engage in an interlocking manner with complementary structures in the patient interface or connection port. To encourage an adequate seal, a pressure activated seal such as a peripheral sealing flange may also be used. It should be understood that additional vent structures may be present; these may also be configured to be removable or alternatively are integrally formed with other components of the patient interface 3000.

To convert the patient interface 3000 to the second use configuration, shown in FIG. 3B, the patient removes the tubes 3310, 3320 of the conduit headgear 3300A from the full-face mask 3010. The conduit headgear is then placed to one side, as it is not required in the second use configuration of this example. It is replaced with a positioning and stabilising structure in the form of a headstrap arrangement 3300B.

In the second use configuration, the air entry ports 3210, 3220 in the patient interface are closed to prevent leaking of pressurised air. The air entry ports 3210, 3220 may be closed with a vent structure 3400 as previously described or sealed off with a plug structure 3500 or stop. This plug structure 3500 may be formed from medical grade plastics material and may be configured with flanges or similar structures, which engage in an interlocking manner with complementary structures in the air entry ports 3210, 3220. As with the vent structure, the plug module may be provided with a pressure activated seal such as a peripheral sealing flange or the like. In forms incorporating a plug module or stop, air exhaled by the patient may be vented by vent structures provided, for example integrally formed, in another part of the patient interface 3000.

In this example of the present technology, the full-face mask 3010 is configured with headgear attachment points 3350 for the headstrap 3300B. The attachment points may take a variety of forms including loops, as shown in FIGS. 3A and 3B but may, depending on the configuration of the headstrap, alternatively be lugs, or buckles.

Figure 9:
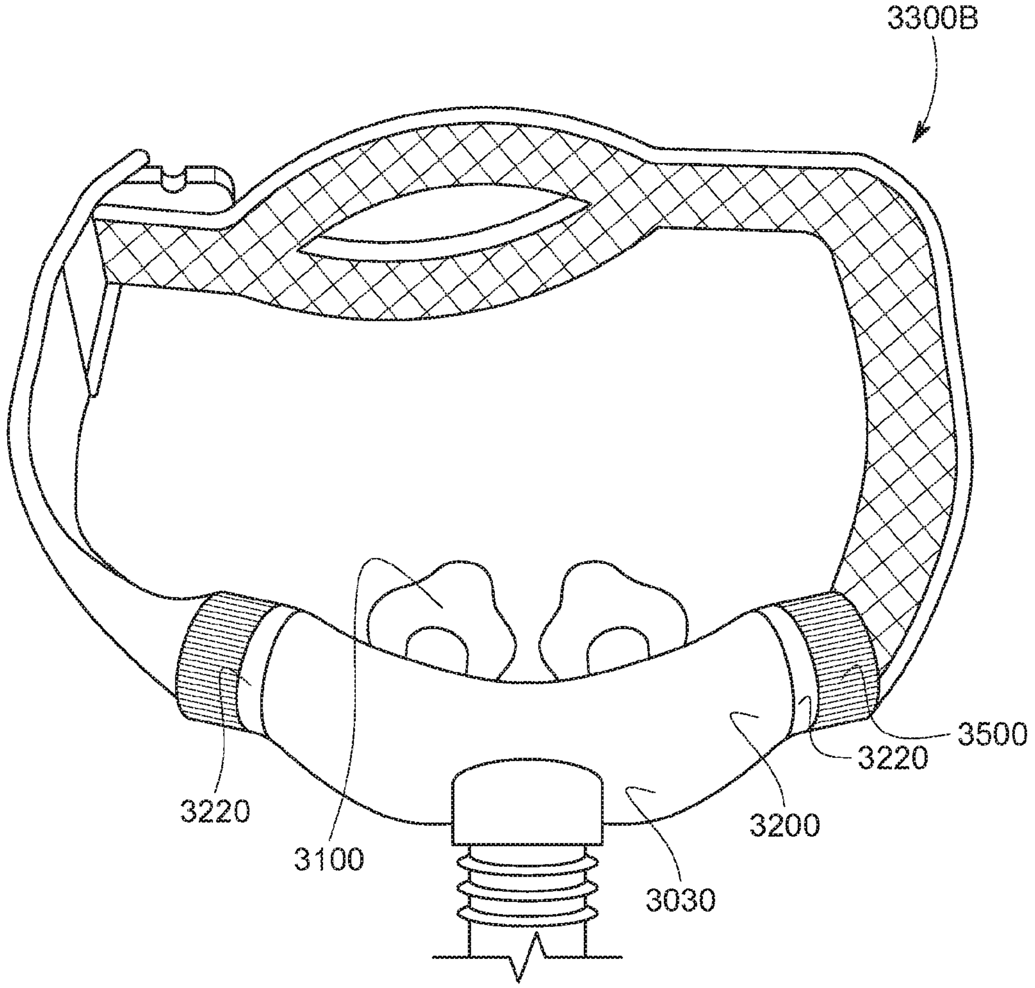
FIG. 9 shows a patient interface in accordance with another form of the present technology.

Another example of the present technology is shown in FIG. 9 in a second use configuration in respect of a patient interface in the form of nasal pillows 3030. In this example, the plug structure 3500 is provided to the ends of the headstrap 3300B used to maintain the seal-forming structure 3100 in place on the patient's face in the second use configuration. The ends of the headstrap are inserted into the air entry ports 3210, 3220 of the plenum chamber 3200. The patient interface in FIG. 9 may alternatively be configured in a first use configuration, in which the headstrap 3300B is interchanged for conduit headgear and the connection port in the anterior side of the plenum chamber (into which an elbow is connected in FIG. 9) is plugged with a plug or vent structure.

In some examples, the patient interface 3000 may be provided with a pair of headgear attachment points 3350; these may be masks with a two-point headgear attachment arrangement. In other examples, the patient interface 3000 may be provided with two opposing pairs of headgear attachment points 3350; these may be masks with a four-point headgear attachment arrangement as shown in FIGS. 3A and 3B.

Figure 10:
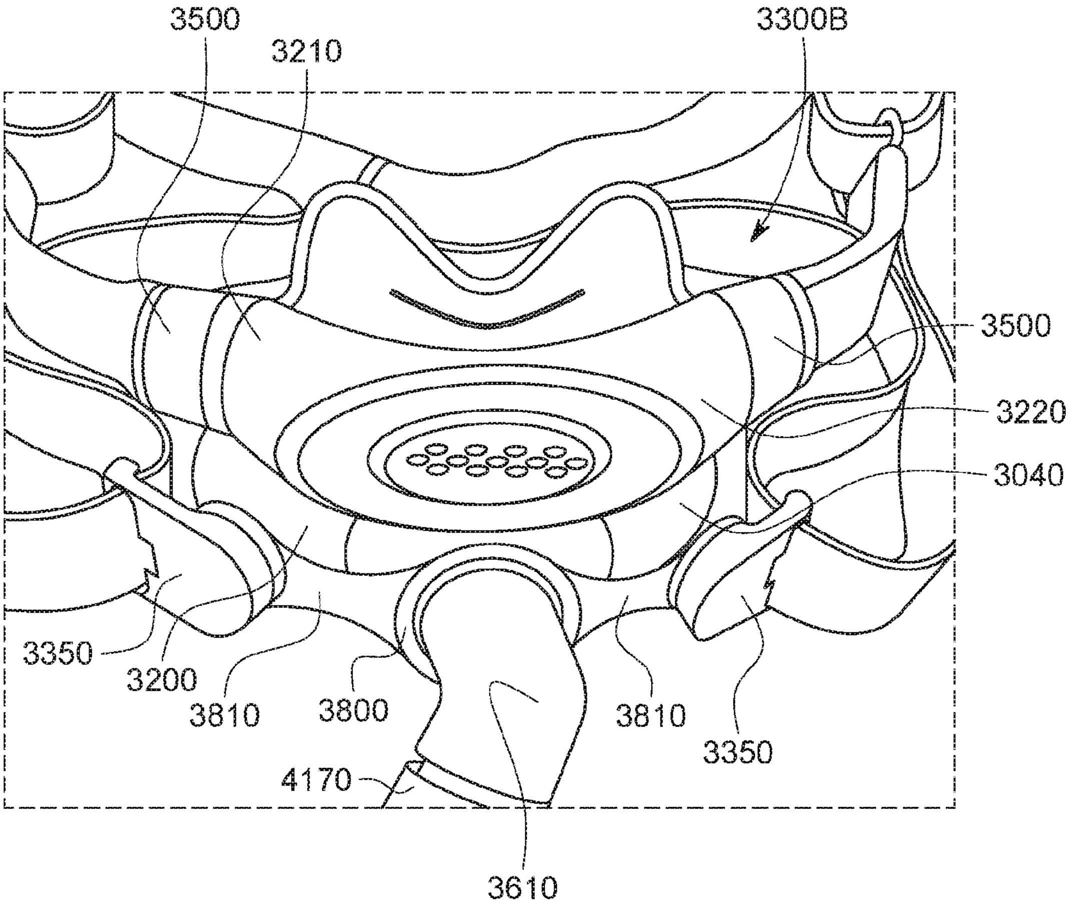
FIG. 10 shows a patient interface in accordance with another form of the present technology.

An alternative example is shown in FIG. 10. In this example, the patient interface is in the form of an oro-nasal mask 3040. Similar to the example of FIG. 9, the air entry ports 3210, 3220 of the plenum chamber 3200 are closed off with plugs 3500 provided to the ends of the headstrap 3300B in the second use configuration. However, in addition, a frame extension 3800 is provided with arms 3810 configured with further attachment points 3350 at their respective ends. The frame extension 3800 allows the use of a headstrap 3300B in the form of a four-point headgear attachment arrangement rather than the two-point headgear attachment arrangement of FIG. 9.

The attachment points 3350 are in the form of push-fit buttons in FIG. 10 but in other examples may be slits through which the straps of the headstrap 3300B may pass and be secured through the use of hook and loop material. Alternatively, the attachment point 3350 may be configured to attach to headstrap 3300B through buckles or clips.

In the example of FIG. 10, the frame extension 3800 is located and held in place by the elbow 3610 of the air circuit 4170. However, in some examples, it may be held in place in a snap-lock or other connection mechanism to the anterior side of the plenum chamber 3200. In other examples, the frame extension 3800 may be provided with means to adjust the length of the arms or alternatively as part of an interchangeable set, in which each frame extension has arms of a different length. This may allow the patient to better adjust, if necessary, force vectors applied to the seal-forming structure when switching from a positioning and stabilising structure in the form of conduit headgear to the form of a headstrap.

In the second use configuration, the downstream end of the air circuit 4170 is inserted into the connection port 3600B on the anterior side of the plenum chamber 3200 of the full-face mask 3010 of FIGS. 3A and 3B, the nasal pillows mask of FIG. 9 or the oro-nasal mask of FIG. 10. This places the downstream end of the air circuit 4170 proximate the lower part of the patient's face and neck, which some patients may prefer to the first use configuration.

This arrangement places the connection port 3600B inferior to the otobasion superior, proximate the face and chin of the patient. In some examples, the straps 3330 of the headstrap arrangement 3300B worn in the second use configuration may be used to close off the air entry ports. In these examples, a portion of the straps may comprise integrated plugs complementary to the air entry ports, and configured to connect to the air entry ports in use.

The patient is able to change the patient interface 3000 shown in FIGS. 3A and 3B, 9 and 10 between the first use and second use configurations by swapping out the respective positioning and stabilising structure 3000 (i.e., conduit headgear 3300A and headstrap arrangement 3300B) and engaging the air circuit 4170 with the appropriate connection port 3600A or 3600B respectively.

The patient interface may also be swapped out if desired. An advantage of the present form of the technology is its relative modularity; by using common connectors and fittings for the tubes of the conduit headgear, air entry ports, and connection ports, the patient interface may be readily interchanged between full-face masks, nasal cushions, nasal pillows and nasal masks, for example.

For some examples of the patient interface 3000, such as full-face or nasal masks, when in the first use configuration, the inferior ends of the tubes 3310, 3320 of the conduit headgear may engage directly with the plenum chamber 3200 as shown in FIGS. 3A and 3B. The relative size of these examples of patient interface are conducive to providing an area sufficiently large for the tubes to engage while still allowing sufficient area for a connection port to be provided to the anterior surface of the plenum chamber.

However, in some other examples of the patient interface, such as nasal cushions which usually have a plenum chamber with an overall smaller surface area, connectors or adaptors may be required to allow connection of the tubes to facilitate delivery of pressurised air to the plenum chamber and seal-forming structure. In such example, the tubes engage with air entry ports in the adaptors, and the adaptors in turn engage with the air entry ports of the plenum chamber 3200.

5.2.9.2 Second Example

Rather than swapping out the positioning and stabilising structure, as with the first example, some patients may prefer to simply swap the placement of the air circuit relative to the patient interface.

In a second example of the present technology, shown in FIG. 4A in a first use configuration, the patient interface 3000 includes a plenum chamber 3200 and seal-forming structure 3100 in the form of a nasal cushion 3020 to which tubes 3310, 3320 are connected. The tubes deliver pressurised air from the air circuit 4170, connected to the elbow 3610 of the connection port 3600A provided to the conduit headgear 3300A forming the positioning and stabilising structure 3300, to the seal-forming structure 3100. Although the illustrated example shows a nasal cushion 3020, in other examples the patient interface may alternatively include a full-face mask, a nasal mask or a nasal pillows.

The tubes 3310, 3320, are each provided with a tab 3380, configured to be engaged with a backstrap 3390. The backstrap 3390 is sufficiently flexible to pass around the back of the patient's head and lie comfortably against the patient's head, even when under tension in use.

The tabs 3380 project away from the tubes in a generally posterior direction. The tabs have slits in them to receive the ends of the backstrap. The strap may be secured to itself after passing through the slits in the tabs, for example, with hook-and-loop fastening material. The strap therefore is able to be adjusted to fit around different head sizes. In some forms of the technology, more than one tab may be provided to provide the patient a range of alternative placement options for the backstrap. This may be helpful for ensuring appropriate application of sealing forces to the face.

In the example of FIGS. 4A and 4B, the tubes 3310, 3320, at their superior ends connect to a crown connector 3360. This allows each of the tubes to be removed separately from the other for cleaning or replacement. The manner of connection to the crown connector may be using the rigid connector 3370 of FIG. 7, as previously described in respect of the first example, but other examples of achieving this connection may include interlocking grooves and pegs, snap-lock fittings, screw threads or the like. In other examples, the conduit headgear may be in the form of that shown in FIG. 3A with the conduit headgear 3300A being a unitary structure with left and right tubes 3310, 3320 meeting at their superior ends, where the connection port 3600A may be located.

Figure 5B:
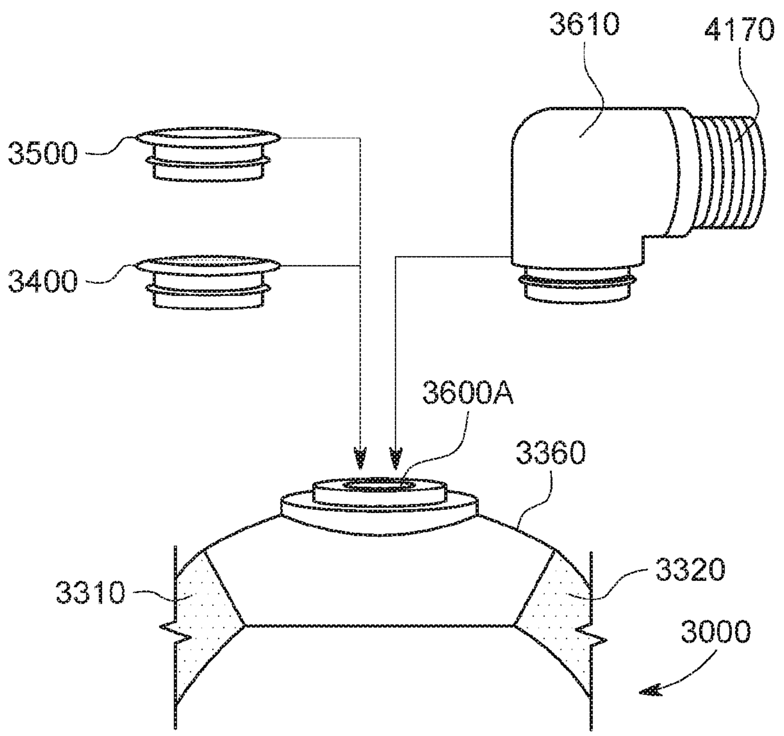
FIG. 5B shows a close up view of the crown connector of the patient interface of FIGS. 4A and 4B.

The nasal mask 3020 is also provided with a connection port 3600B on its anterior side as shown in a close up view in FIG. 5A. As shown in FIG. 5B, the crown connector 3360 also includes a connection port 3600A. The respective connection ports 3600A, 3600B may be configured and arranged with identical or similar engagement mechanisms, such as snap-lock or push-fit fittings, that are complementary to the fittings provided to the downstream end of the air circuit 4170. This allows the air circuit to be inserted and sealingly engage with one or the other of the two connection ports 3600A, 3600B. In the illustrated examples of FIGS. 5A and 5B, the engagement mechanisms of the connection ports 3600A, 3600B, are complementary to an end of the elbow 3160. In these examples, the downstream end of the air circuit is connected to the elbow 3160, which in turn is inserted and sealing engaged with one or the other of the two connection ports 3600A, 3600B.

When one of the two connection ports 3600A, 3600B receives the air circuit 4170, the other connection port is open. This may compromise the delivery of pressurised air to the patient. To prevent this, a vent structure 3400 or plug 3500 is inserted into the open connection port. In one form, the when one of the two connection ports 3600A, 3600B receives the air circuit 4170, the other connection port is substantially sealed with a closure.

In the first use configuration, when the air circuit delivers pressurised air to the patient interface via the elbow 3610 and tubes 3310, 3320, the vent structure 3400 or plug 3500 is inserted into the connection port 3600B in the plenum chamber 3200 of the nasal mask 3020 to ensure minimal or no loss of pressurised air from the patient interface (other than that exiting through the vent structure).

In the second use configuration, when the air circuit is delivering pressurised air to the patient interface via the nasal mask, the vent structure 3400 or plug 3500 is inserted into the connection port 3600A at the crown connector 3360.

As previously described, the respective connection ports 3600A, 3600B may be configured and arranged with identical engagement mechanisms to facilitate the connection to the air circuit. In some examples, the vent structure or plug is provided with complementary engagement mechanisms. This allows the same vent structure 3400 or plug 3500 to be interchangeable between the connection ports 3600A, 3600B, advantageously reducing the number of components that need to be manufactured and supplied as part of the patient interface 3000.

To convert the patient interface 3000 to the second use configuration shown in FIG. 4B, the patient simply removes the elbow 3610 from the crown connector 3360, replacing it with a vent structure 3400 or plug 3500. The elbow 3610 is then engaged with the connection port 3600B of the nasal cushion 3020.

5.2.9.3 Third Example

In a third example, shown in FIG. 6, the tubes 3310, 3320 of the conduit headgear 3300A may engage with the patient interface 3000, in the form of a nasal cushion 3020, such that the tubes may be re-arranged between the first use and second use configurations. This may be advantageous since the patient may not need to completely disengage the air circuit 4170 from the connection port 3600A of the patient interface.

In this example, while the conduit headgear 3300A is worn in the first use configuration as per FIG. 4A, in the second use configuration of FIG. 6, the conduit headgear, although still in use for delivering pressurised air to the seal forming structure 3100 of the nasal cushion 3020, has been substantially inverted.

In this example, the manner of engagement of the tubes 3310, 3320 of the conduit headgear 3300A with the plenum chamber 3200 is such that the tubes may swivel or otherwise rotate relative to the nasal cushion 3020.

Figure 8A:
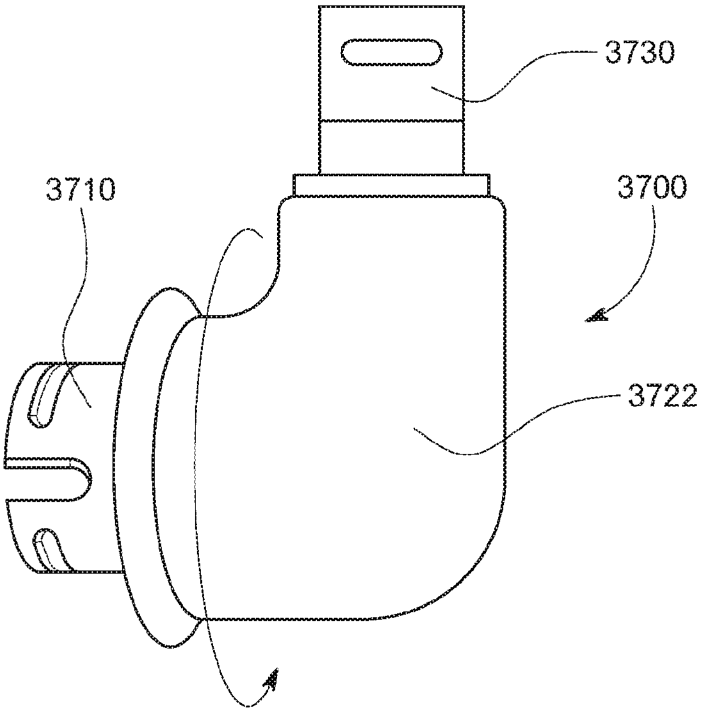
FIG. 8A shows an adaptor for a tube of a conduit headgear for use with the form of the present technology of FIG. 6.

For example, in FIG. 8A, the air entry ports of the patient interface may be provided with an adaptor 3700 that includes a swivel ring 3710. The ring is inserted and locked, through appropriate interlocking mechanisms, into the air entry ports of the patient interface. The adaptor comprises an elbow 3722 with a receiving portion 3730 into which the inferior end of the connector of the tube may be fitted. Once the ring is located and locked in place within the air entry port, the tube is then able to swivel within the ring.

Figure 8B:
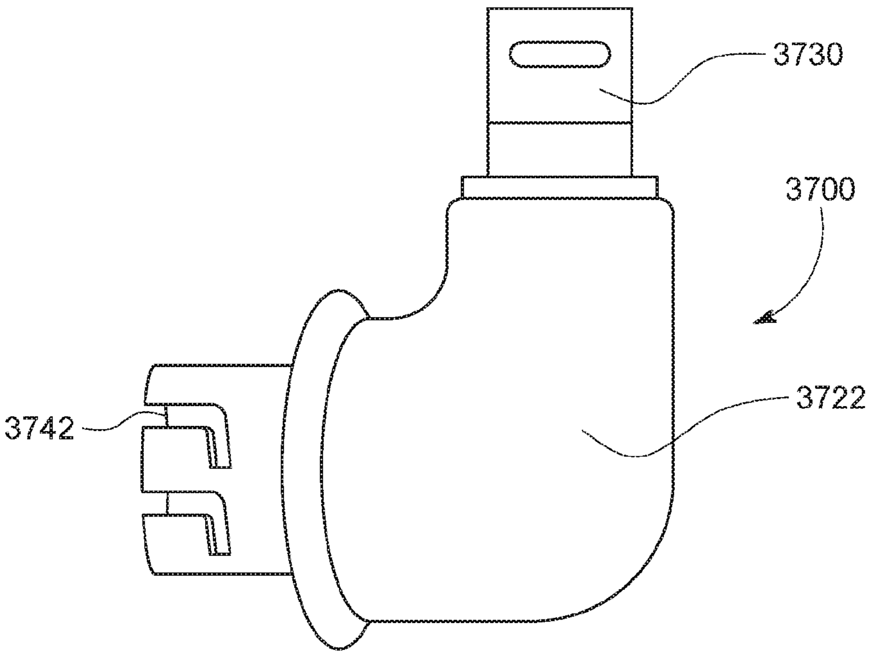
FIG. 8B shows an alternative adaptor for a tube of a conduit headgear for use with the form of the present technology of FIG. 6.

In another example, in FIG. 8B, the manner of engagement of the tubes of the conduit headgear with the plenum chamber is such that two or more discrete positions may be achieved, for example by detaching and re-attaching the tubes of the conduit headgear to the plenum chamber. For instance, the adaptor 3700 may be configured as a one-piece elbow 3722 with an end configured to be inserted and locked into the air entry ports provided with a series of axially aligned slots 3742. These slots engage with co-operating pegs provided to the interior surface of the air entry port of the patient interface. Other ways of engaging the tubes with the interface may be envisaged; for example, the tubes may bear the pegs and the patient interface provided with the slots. This provides a series of positions for locating the tube relative to the patient interface. Depending on the desired orientation of the conduit headgear, the patient inserts the tubes into the patient interface at the desired position, aligning the respective interlocking parts. In this example, there may only be two positions, i.e. two sets of slots/pegs corresponding to a "tube up" configuration and "tube down" configuration respectively. However, in other examples, further positions could be provided. This may help optimise fit of the conduit headgear when being worn in a tube up configuration.

It will be understood that, in this example, the conduit headgear 3300A is the first positioning and stabilising structure. However, when in the second use configuration a force is still required to be applied to ensure the seal-forming structure 3100 remains in place on the patient's face. Therefore, when the conduit headgear 3300 is in the inverted state of FIG. 6, a second positioning and stabilising structure in the form of a headstrap arrangement 3300B is required to ensure the seal-forming structure 3100 remains in sealing contact with the patient's face.

The headstrap arrangement 3300B includes one or more straps 3330 that are worn about the head of the patient above the otobasion superior. In contrast to the embodiment of the headstrap arrangement of FIG. 3B, in FIG. 6, the headstrap arrangement 3300B only attaches to the nasal cushion 3020 at two headgear attachment points 3350.

In this second use configuration, the connection port 3600A has been moved from its original position superior to the otobasion superior to a position where it is inferior to the otobasion superior. In the second use configuration, the connection port 3600A and air circuit 4170 is proximate the chin and neck of the patient.

5.2.9.4 Closure Examples

In the first use configuration, when the air circuit delivers pressurised air to the patient interface via the elbow 3610 and tubes 3310, 3320, the connection port 3600B in the plenum chamber 3200 of the nasal mask 3020 is closed (e.g., using a vent structure 3400, plug structure 3500 or a closure 3786) to ensure minimal or no loss of pressurised air from the patient interface (other than that exiting through the vent structure, if present).

In the second use configuration, when the air circuit is delivering pressurised air to the patient interface via the nasal mask, the connection port 3600A at the crown connector 3360 is closed (e.g., using a vent structure 3400, plug structure 3500 or a closure 3786) to ensure minimal or no loss of pressurised air from the patient interface (other than that exiting through the vent structure, if present).

As previously described, the respective connection ports 3600A, 3600B may be configured and arranged with identical or similar engagement mechanisms to facilitate the connection to the air circuit.

The engagement mechanisms, such as snap-lock or push-fit fittings, are complementary to the fittings provided to the downstream end of the air circuit 4170, allowing the air circuit to be inserted and sealingly engage with one or the other of the two connection ports 3600A, 3600B. In the illustrated examples of FIGS. 4A and 4B, the engagement mechanisms of the connection ports 3600A, 3600B, are complementary to an end of the elbow 3160. In these examples, the downstream end of the air circuit is connected to the elbow 3160, which in turn is inserted and sealing engaged with one or the other of the two connection ports 3600A, 3600B.

The connection ports 3600A and 3600B may comprise a closure 3786 covering an opening into which the downstream end of the air circuit may be inserted. The closure is moveable, either by the patient or by the downstream end (or elbow) of the air circuit such that it can change from a closed condition, where the connection port is substantially sealed (in some examples, there may be some functionality for venting exhaled carbon dioxide) to an open condition, where pressurised air is delivered to the tubes of the conduit headgear and into the patient's airways. The closure may be configured in a number of ways.

Figure 11:
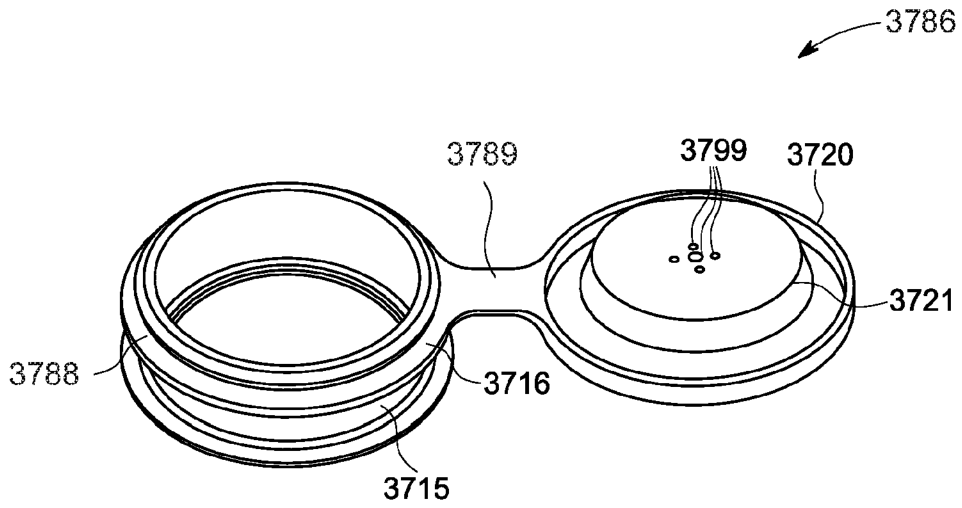
FIG. 11 shows a first example of a closure for a patient interface in accordance with another form of the present technology.

In a first example of the closure 3786, shown in an open condition in FIG. 11, it may be in the form of a rigid ring 3788 defining a mouth for the closure. The ring is made, for example, from polypropylene, polycarbonate, nylon or the like. In use, the lower portion 3715 of the ring 3788 is disposed within the connection port. The ring 3788 may be a separate structure, as shown in FIG. 11, inserted by the patient as required or alternatively may be integrally formed with the connection port (e.g., connection ports 3600A, 3600B).

Circumscribing the rigid ring 3788 is a loop 3716 to which a lid closure 3720 is connected by a hinge portion 3789. The hinge portion 3789 may be formed of a soft, deformable plastics material allowing the closure to be placed in a closed condition. The patient may simply mate the inner surface 3721 of the lid with the rigid ring 3788 of the closure 3786. In some examples, the lid may be a separate structure, not connected to the ring. In this example, the ring 3788 may be provided without the hinge portion 3789. In some examples, the hinge portion 3789 may be removably coupled to the lid closure 3720 and/or the ring 3788.

The lid is provided with a plurality of apertures; these serve as vent holes 3799 to vent carbon dioxide exhaled by the patient but without allowing undue volumes of pressurised air to be lost. The number of apertures and their dimensions may vary according to the desired volume of exhaled gases to be vented. They need to be sufficient to reduce rebreathing of exhaled $CO_2$ by the patient while maintaining the therapeutic pressure in the plenum chamber in use.

Figure 12A:
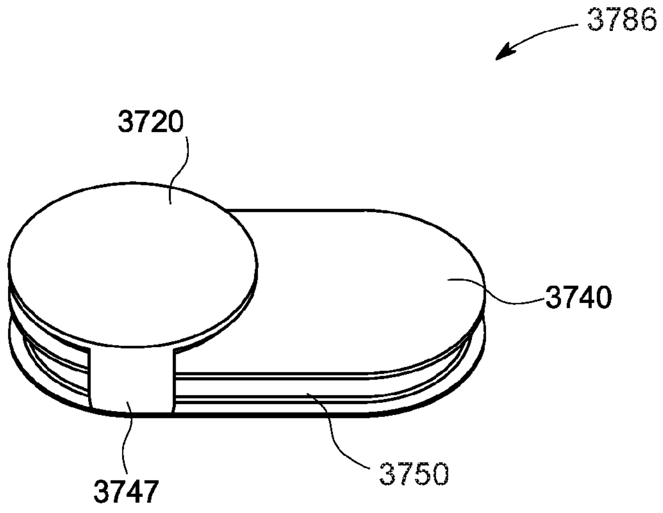
FIG. 12A shows a further example of a closure for a patient interface in accordance with another form of the present technology.
Figure 12B:
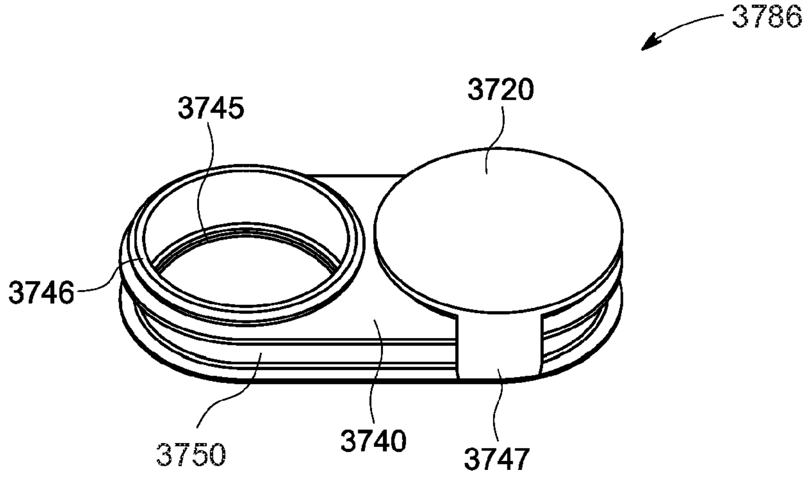
FIG. 12B shows the closure of FIG. 12A in an open condition.

FIGS. 12A and 12B show other examples of a closure 3786 suitable for use with the present technology, in a closed condition and open condition respectively. In this example, the closure 3786 is in the form of an elongate body 3740 comprising, at one end, an opening 3745 circumscribed by a raised mouth 3746. The elongate body 3740 may be formed, for example, from polypropylene, polycarbonate, nylon or the like. The closure 3786 also comprises a circular lid closure 3720, with flanges 3747 extended inferiorly, similarly formed from polypropylene, polycarbonate, nylon or the like. The sides of the body may be configured with a track 3750 or rail to which the flanges 3747 of the lid engage. In this example, the patient simply slides the lid along the track to place the closure, in its closed condition in FIG. 7A to an open condition as shown in FIG. 12B. The inferior side (not visible in FIGS. 12A and 12B) of the lid enclosure 3720 may include a layer of silicone or the like to assist in sealing the mouth 3745 of the closure 3786.

Although shown in FIGS. 12A and 12B with the mouth 3745 favouring one end of the body 3740, the mouth 3745 may be more centrally orientated. This may require the body itself to be larger, to ensure clearance for the lid 3720 when it is slid from the closed condition to the open condition. In some examples, the mouth 3745 may be provided in the centre of the body 3740, allowing for the lid 3720 to be moved to either side of the mouth 3745. Alternatively, the lid 3720 may be formed from two halves, each half favouring one end of the body. The patient slides the two halves together to meet over the mouth.

In some examples, the ends of the track 3750 may include a stop in the form of a moulded peg or the like to ensure the lid 3720 does not become disengaged from the body should it move too far along the track 3750.

In some examples, the lid 3720 may be provided with a plurality of apertures arranged and dimensioned for venting purposes. In other examples, the raised mouth of the ring may be formed with a series of notches extending posterior of the top surface of the mouth. In this example, while the lid may be able to form a seal with the top surface of the mouth, the notches serve to allow exhaled gases to be vented. It will be appreciated that the flanges of the lid may be arranged to ensure sufficient clearance of the lid as it is moved from the closed and open conditions. The dimensions of the notches need to be sufficient to reduce rebreathing of exhaled $CO_2$ by the patient while maintaining the therapeutic pressure in the plenum chamber in use.

Figure 13A:
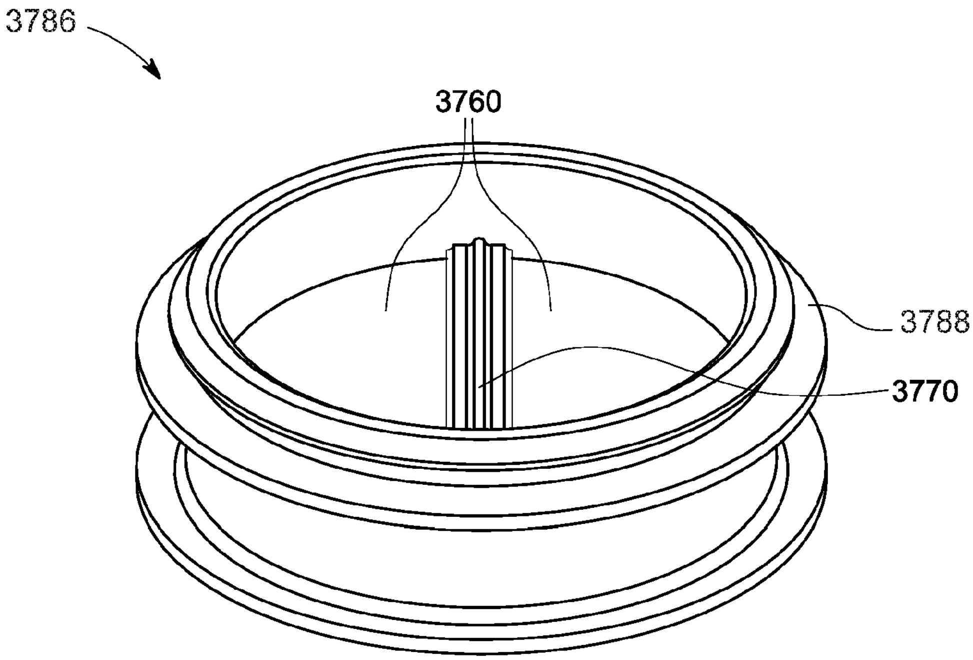
FIG. 13A shows a further example of a closure for a patient interface in accordance with another form of the present technology.
Figure 13B:
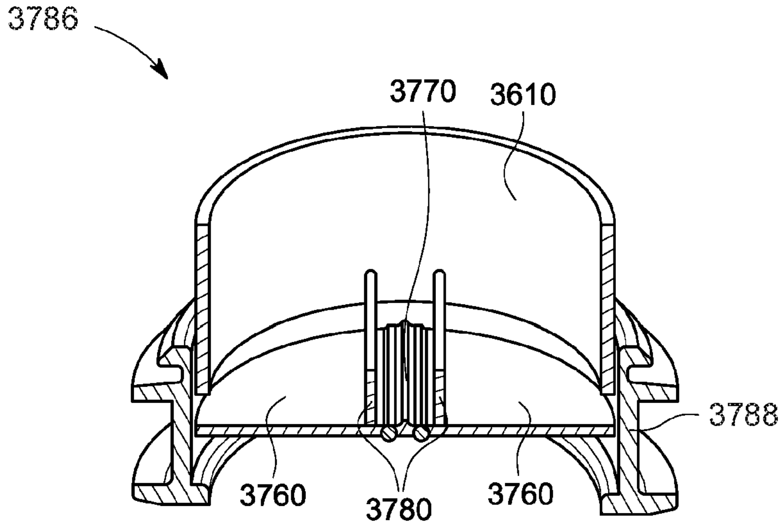
FIG. 13B shows a cross section of the closure of FIG. 13A with an elbow of an air circuit.
Figure 13C:
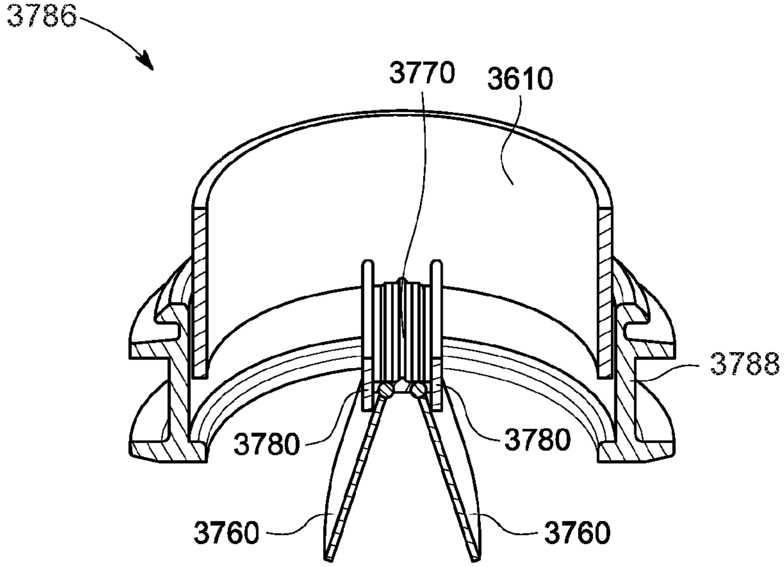
FIG. 13C shows a cross section of the closures of FIGS. 13A and 13B in an open condition.

In the examples of FIGS. 11, 12A, and 12B, the closure 3786 is manipulated by the patient in order to place it in the desired closed or open condition. In some examples, the act of inserting the downstream end of the air circuit into the connection ports may place the closure into an open condition from a closed condition. FIGS. 13A to 13C shows one such example.

In this example, the closure 3786 is in the form of a ring 3788, best seen in FIG. 13A, either integrally formed with the connection port or as a separate component inserted by the patient. Within the interior of the ring 3788 is disposed a pair of closure flaps 3760. These closure flaps are pivotally hinged to a strut 3770 spanning the ring. This strut may be arranged to assist in the direction of pressurised air; for example, the strut may act as a flow divider, assisting in directing separate flow paths of pressurised air to the left and right tubes of conduit headgear. In these examples, the strut may be aligned to best effect this division of air flow. For example, the strut may be arranged to divide the opening of the closure into left and right side portions, corresponding with the left and right tubes of the conduit headgear.

Figure 14A:
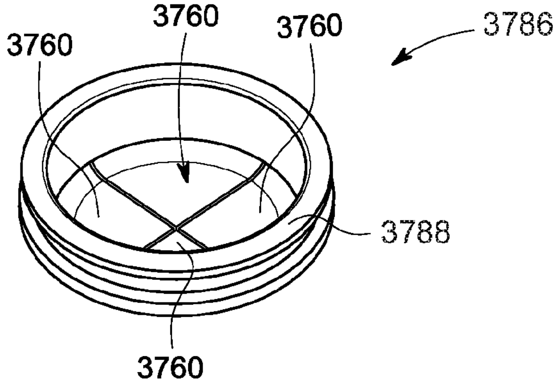
FIG. 14A shows a further example of a closure for a patient interface in accordance with another form of the present technology.
Figure 14B:
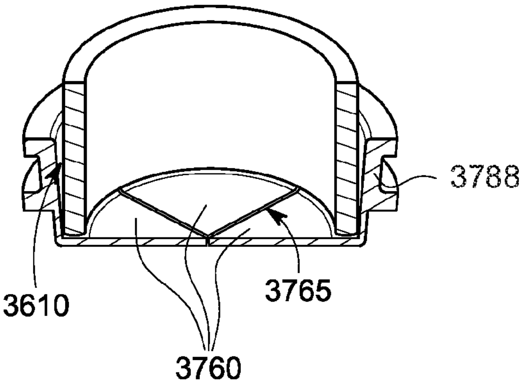
FIG. 14B shows a cross section of the closure of FIG. 14A in a closed condition.
Figure 14C:
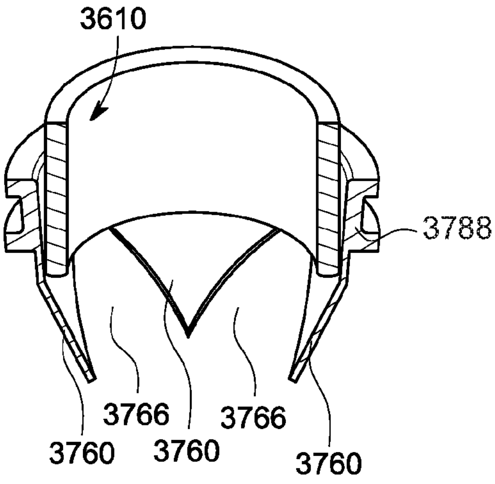
FIG. 14C shows a cross section of the closures of FIGS. 14A and 14B in an open condition.

However, in other examples, the closure flaps 3760 may be pivotally hinged or otherwise mounted to the perimeter of the ring 3788 as shown in FIGS. 14A to 14C. Furthermore, the number of closure flaps may vary. In one example, there may be a single, substantially circular closure flap hinged to the perimeter of the ring by one edge. In other examples, such as that shown in FIGS. 14A to 14C (FIGS. 14B and 14C being cross-sections of the closure of FIG. 14A), there may be four (or more) closure flaps 3760, arranged equidistant around the perimeter of the ring 3788.

Figure 14D:
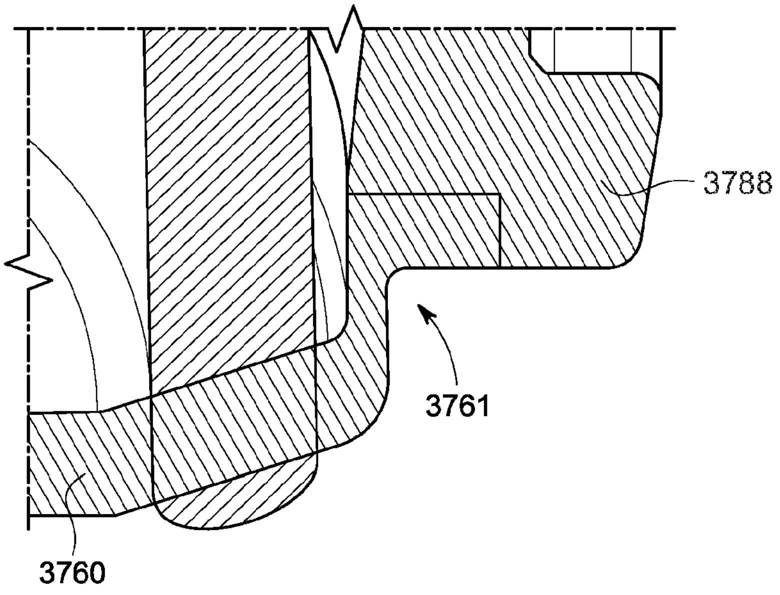
FIG. 14D shows a cross section of the closures of FIGS. 14A-14C including a hinge for closure flaps.

In an example, in the closed condition as shown in FIG. 14B, the closure flaps 3760 are arranged such that a small slit or gap 3765 is provided between adjacent flaps. These may provide some venting functionality. The closure flaps 3760 may be mounted to the ring 3788 such that a thin section functions as a hinge 3761 as shown in FIG. 14D, such that the closure flaps may move from a closed condition to an open condition.

In an open condition as shown in FIG. 14C, the closure flaps are biased to an open condition by the elbow 3610 of the air circuit 4170. This create channels 3766 therebetween to allow for airflow into left and right tubes of the conduit headgear, at a therapeutically effective air pressure. The flow of pressurised air may be optimized by aligning the channels 3766 created by the open closure flaps 3760 with the direction of air flow in the tubes of the conduit headgear to minimize flow impedance. In another example, the orientation of the channels may be determined with respect to one or more of (1) the axial direction of the downstream end portion of the air circuit (the elbow in FIGS. 14B and 14C), (2) the axial direction of the left and right tube of the conduit headgear, (3) the direction of air flow in the tube of the conduit headgear. In a further example, the orientation of the flaps is may be adjusted manually. For example, the ring 3788 may be configured to be rotatable within the connection port to change the axial orientation of the closure flaps 3760.

In FIG. 13A, the closure flaps 3760 are arranged such that the closure is in a closed condition. For venting purposes, in one example, apertures (not shown in FIGS. 13A to 13C) may be provided to the closure flaps. As described for previous examples of the closure, the number and dimensions of the apertures may vary according to the desired volume of exhaled gases to be vented. In another example, the closure flaps may be mounted to the ring such that there is a gap or slit (not shown) between adjacent flaps and/or the ring 3788 and/or the strut 3770. The gap or slit serves as a vent for exhaled carbon dioxide.

In FIGS. 13B and 13C, the interaction of the closure flaps 3760 with the downstream end portion of the air circuit (in this example, the elbow 3610) can be seen. The bore of the elbow comprises an activation mechanism in the form of a pair of wedges 3780 arranged to span the bore. In this example, the separation of the wedges is to ensure clearance for the strut 3770 as the elbow 3610 advances into the closure 3786. The wedges 3780 bear against the closure flaps 3760 and as the elbow 3610 is advanced further into the closure, pivot them about the strut 3770 and bias them from a closed condition to an open condition, as shown in FIG. 13C, allowing passage of pressurised air to enter the connection port.

In examples where the closure flaps are mounted by an outer edge to the ring such as that of FIGS. 9A-9C, it may not be necessary for the bore of the elbow 3610 to be configured with wedges. Instead, the activation mechanism is the perimeter of the bore, which contacts the closure flaps 3760 and bias them open as the elbow is advanced.

While the ring 3788 itself may be formed from polypropylene, polycarbonate, nylon or the like, in some examples, the closure flaps may be formed from a less rigid plastics material, such as liquid silicone rubber of an appropriate shore hardness. The manner in which the closure flaps are connected to the strut (or perimeter of the ring) are such that the connected portion of the closure flap functions as a living hinge. In alternative forms, the closure flaps may be more rigid but connected via specific hinge structure to the strut (or perimeter of the ring).

Figure 15:
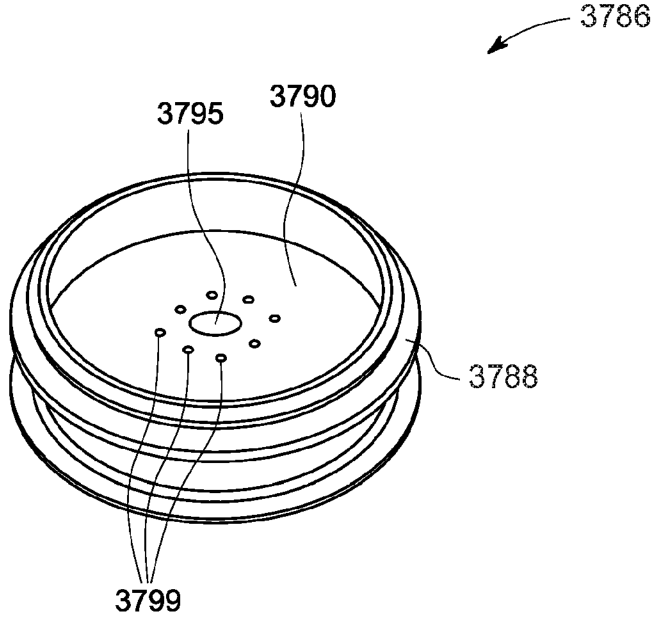
FIG. 15 shows a further example of a closure for a patient interface in accordance with another form of the present technology.

An alternative example in which the action of inserting the downstream end portion of the air circuit into the connection ports may place the closure into an open condition from a closed condition is shown in FIG. 15. In this example, the closure is in the form of a ring 3788, much as described in respect of the previous example. However, the interior of the closure is spanned by a seal 3790 in the form of a layer of stretchable elastic material, such as rubber or silicone having an appropriately low shore hardness.

FIG. 15 shows this seal 3790 in its closed condition. At its centre, the seal includes a central aperture 3795. When the downstream end of the air circuit, for example the elbow, is inserted into the closure 3786, the seal becomes distended and stretched. This increases the overall dimensions of the central aperture 3795 sufficiently to receive the downstream end of the air circuit and/or allow a sufficient amount of pressurised air to enter the connection port for therapy purposes. This biases the closure 3786 from an open condition to a closed condition. On removal of the downstream end of the circuit, the seal returns to its original closed condition. The layer of stretchable elastic material may also include additional vent holes 3799 surrounding the central aperture 3795 for venting the required volume of carbon dioxide. However, the size of the central aperture 3795 may be sufficient for this purpose in its own right.

In the examples of FIGS. 11 to 15, to convert the patient interface 3000 from the first use configuration of FIG. 4A to the second use configuration such as that shown in FIG. 4B, the patient simply removes the elbow 3610 from the connection port 3600A or the crown connector 3360 and then engages it with the connection port 3600B of the nasal cushion 3020. To achieve this, the patient may need to move the closure 3786 of the nasal cushion 3020 from a closed condition to an open condition. Since the connection port 3600A of the crown connector 3360 is now open, the closure of the crown connector needs to be moved from an open condition to a closed condition. Alternatively, the action of inserting the elbow 3610 may adjust the closure from a closed condition to the open condition. Removal of the elbow from the connection port allows the closure to self-adjust to a closed condition.

It should be appreciated that the connection ports of the patient interface may be provided such that each has a different type of closure. For example, the connection port 3600A provided to the conduit headgear may be provided with a closure such as that described in FIGS. 13A-14D while the connection port 3600B of the plenum chamber is provided with a closure such as that described in FIGS. 11 and 12A. While the patient interface is being worn, the patient may find it easier to manipulate closures on the plenum chamber than the closure provided to the conduit headgear.

6 GLOSSARY

For the purposes of the present technology disclosure, in certain forms of the present technology, one or more of the following definitions may apply. In other forms of the present technology, alternative definitions may apply.

6.1 General

Air: In certain forms of the present technology, air may be taken to mean atmospheric air, and in other forms of the present technology air may be taken to mean some other combination of breathable gases, e.g. atmospheric air enriched with oxygen.

Ambient: In certain forms of the present technology, the term ambient will be taken to mean (i) external of the treatment system or patient, and (ii) immediately surrounding the treatment system or patient.

Automatic Positive Airway Pressure (APAP) therapy: CPAP therapy in which the treatment pressure is automatically adjustable, e.g. from breath to breath, between minimum and maximum limits, depending on the presence or absence of indications of SDB events.

Continuous Positive Airway Pressure (CPAP) therapy: Respiratory pressure therapy in which the treatment pressure is approximately constant through a respiratory cycle of a patient. In some forms, the pressure at the entrance to the airways will be slightly higher during exhalation, and slightly lower during inhalation. In some forms, the pressure will vary between different respiratory cycles of the patient, for example, being increased in response to detection of indications of partial upper airway obstruction, and decreased in the absence of indications of partial upper airway obstruction.

Flow therapy: Respiratory therapy comprising the delivery of a flow of air to an entrance to the airways at a controlled flow rate referred to as the treatment flow rate that is typically positive throughout the patient's breathing cycle.

Patient: A person, whether or not they are suffering from a respiratory condition.

Pressure: Force per unit area. Pressure may be expressed in a range of units, including $cmH_2O$, g-f/$cm^2$ and hectopascal. 1 $cmH_2O$ is equal to 1 g-f/$cm^2$ and is approximately 0.98 hectopascal (1 hectopascal=100 Pa=100 N/$m^2$=1 millibar~0.001 atm). In this specification, unless otherwise stated, pressure is given in units of $cmH_2O$.

The pressure in the patient interface is given the symbol Pm, while the treatment pressure, which represents a target value to be achieved by the interface pressure Pm at the current instant of time, is given the symbol Pt.

Respiratory Pressure Therapy (RPT): The application of a supply of air to an entrance to the airways at a treatment pressure that is typically positive with respect to atmosphere.

Ventilator: A mechanical device that provides pressure support to a patient to perform some or all of the work of breathing.

6.2 Materials

Silicone or Silicone Elastomer: A synthetic rubber. In this specification, a reference to silicone is a reference to liquid silicone rubber (LSR) or a compression moulded silicone rubber (CMSR). One form of commercially available LSR is SILASTIC (included in the range of products sold under this trademark), manufactured by Dow Corning. Another manufacturer of LSR is Wacker. Unless otherwise specified to the contrary, an exemplary form of LSR has a Shore A (or Type A) indentation hardness in the range of about 35 to about 45 as measured using ASTM D2240.

Polycarbonate: a thermoplastic polymer of Bisphenol-A Carbonate.

6.3 Mechanical Properties

Resilience: Ability of a material to absorb energy when deformed elastically and to release the energy upon unloading.

Resilient: Will release substantially all of the energy when unloaded. Includes e.g. certain silicones, and thermoplastic elastomers.

Hardness: The ability of a material per se to resist deformation (e.g. described by a Young's Modulus, or an indentation hardness scale measured on a standardised sample size).

'Soft' materials may include silicone or thermo-plastic elastomer (TPE), and may, e.g. readily deform under finger pressure.

'Hard' materials may include polycarbonate, polypropylene, steel or aluminium, and may not e.g. readily deform under finger pressure.

Stiffness (or rigidity) of a structure or component: The ability of the structure or component to resist deformation in response to an applied load. The load may be a force or a moment, e.g. compression, tension, bending or torsion. The structure or component may offer different resistances in different directions. The inverse of stiffness is flexibility.

Floppy structure or component: A structure or component that will change shape, e.g. bend, when caused to support its own weight, within a relatively short period of time such as 1 second.

Rigid structure or component: A structure or component that will not substantially change shape when subject to the loads typically encountered in use. An example of such a use may be setting up and maintaining a patient interface in sealing relationship with an entrance to a patient's airways, e.g. at a load of approximately 20 to 30 $cmH_2O$ pressure.

As an example, an I-beam may comprise a different bending stiffness (resistance to a bending load) in a first direction in comparison to a second, orthogonal direction. In another example, a structure or component may be floppy in a first direction and rigid in a second direction.

6.4 Anatomy of the Face

Auricle: The whole external visible part of the ear.

(nose) Bony framework: The bony framework of the nose comprises the nasal bones, the frontal process of the maxillae and the nasal part of the frontal bone.

(nose) Cartilaginous framework: The cartilaginous framework of the nose comprises the septal, lateral, major and minor cartilages.

Frankfort horizontal plane: A line extending from the most inferior point of the orbital margin to the left tragion. The tragion is the deepest point in the notch superior to the tragus of the auricle.

Lip, lower (labrale inferius):

Lip, upper (labrale superius):

Nares (Nostrils): Approximately ellipsoidal apertures forming the entrance to the nasal cavity. The singular form of nares is naris (nostril). The nares are separated by the nasal septum.

Otobasion inferior: The lowest point of attachment of the auricle to the skin of the face.

Otobasion superior: The highest point of attachment of the auricle to the skin of the face.

Sagittal plane: A vertical plane that passes from anterior (front) to posterior (rear). The midsagittal plane is a sagittal plane that divides the body into right and left halves.

6.5 Anatomy of the Skull

Frontal bone: The frontal bone includes a large vertical portion, the squama frontalis, corresponding to the region known as the forehead.

Mandible: The mandible forms the lower jaw. The mental protuberance is the bony protuberance of the jaw that forms the chin.

Maxilla: The maxilla forms the upper jaw and is located above the mandible and below the orbits. The frontal process of the maxilla projects upwards by the side of the nose, and forms part of its lateral boundary.

Nasal bones: The nasal bones are two small oblong bones, varying in size and form in different individuals; they are placed side by side at the middle and upper part of the face, and form, by their junction, the "bridge" of the nose.

Nasion: The intersection of the frontal bone and the two nasal bones, a depressed area directly between the eyes and superior to the bridge of the nose.

Occipital bone: The occipital bone is situated at the back and lower part of the cranium. It includes an oval aperture, the foramen magnum, through which the cranial cavity communicates with the vertebral canal. The curved plate behind the foramen magnum is the squama occipitalis.

Orbit: The bony cavity in the skull to contain the eyeball.

Parietal bones: The parietal bones are the bones that, when joined together, form the roof and sides of the cranium.

Temporal bones: The temporal bones are situated on the bases and sides of the skull, and support that part of the face known as the temple.

Zygomatic bones: The face includes two zygomatic bones, located in the upper and lateral parts of the face and forming the prominence of the cheek.

6.6 Patient Interface

Anti-asphyxia valve (AAV): The component or sub-assembly of a mask system that, by opening to atmosphere in a failsafe manner, reduces the risk of excessive $CO_2$ rebreathing by a patient.

Elbow: An elbow is an example of a structure that directs an axis of flow of air travelling therethrough to change direction through an angle. In one form, the angle may be approximately 90 degrees. In another form, the angle may be more, or less than 90 degrees. The elbow may have an approximately circular cross-section. In another form the elbow may have an oval or a rectangular cross-section. In certain forms an elbow may be rotatable with respect to a mating component, e.g. about 360 degrees. In certain forms an elbow may be removable from a mating component, e.g. via a snap connection. In certain forms, an elbow may be assembled to a mating component via a one-time snap during manufacture, but not removable by a patient.

Frame: Frame will be taken to mean a mask structure that bears the load of tension between two or more points of connection with a headgear. A mask frame may be a non-airtight load bearing structure in the mask. However, some forms of mask frame may also be air-tight.

Headgear: Headgear will be taken to mean a form of positioning and stabilizing structure designed for use on a head. For example the headgear may comprise a collection of one or more struts, ties and stiffeners configured to locate and retain a patient interface in position on a patient's face for delivery of respiratory therapy. Some ties are formed of a soft, flexible, elastic material such as a laminated composite of foam and fabric. Alternatively, the headgear may be in the form of one or two gas delivery tubes which may conform somewhat to the shape of the head.

Membrane: Membrane will be taken to mean a typically thin element that has, preferably, substantially no resistance to bending, but has resistance to being stretched.

Plenum chamber: a mask plenum chamber will be taken to mean a portion of a patient interface having walls at least partially enclosing a volume of space, the volume having air therein pressurised above atmospheric pressure in use. A shell may form part of the walls of a mask plenum chamber.

Seal: May be a noun form ("a seal") which refers to a structure, or a verb form ("to seal") which refers to the effect. Two elements may be constructed and/or arranged to 'seal' or to effect 'sealing' therebetween without requiring a separate 'seal' element per se.

Shell: A shell will be taken to mean a curved, relatively thin structure having bending, tensile and compressive stiffness. For example, a curved structural wall of a mask may be a shell. In some forms, a shell may be faceted. In some forms a shell may be airtight. In some forms a shell may not be airtight.

Swivel (noun): A subassembly of components configured to rotate about a common axis, preferably independently, preferably under low torque. In one form, the swivel may be constructed to rotate through an angle of at least 360 degrees. In another form, the swivel may be constructed to rotate through an angle less than 360 degrees. When used in the context of an air delivery conduit, the sub-assembly of components preferably comprises a matched pair of cylindrical conduits. There may be little or no leak flow of air from the swivel in use.

Tie (noun): A structure designed to resist tension.

Vent: (noun): A structure that allows a flow of air from an interior of the mask, or conduit, to ambient air for clinically effective washout of exhaled gases. For example, a clinically effective washout may involve a flow rate of about 10 litres per minute to about 100 litres per minute, depending on the mask design and treatment pressure.

7 OTHER REMARKS

A portion of the disclosure of this patent document contains material which is subject to copyright protection. The copyright owner has no objection to the facsimile reproduction by anyone of the patent document or the patent disclosure, as it appears in Patent Office patent files or records, but otherwise reserves all copyright rights whatsoever.

Unless the context clearly dictates otherwise and where a range of values is provided, it is understood that each intervening value, to the tenth of the unit of the lower limit, between the upper and lower limit of that range, and any other stated or intervening value in that stated range is encompassed within the technology. The upper and lower limits of these intervening ranges, which may be independently included in the intervening ranges, are also encompassed within the technology, subject to any specifically excluded limit in the stated range. Where the stated range includes one or both of the limits, ranges excluding either or both of those included limits are also included in the technology.

Furthermore, where a value or values are stated herein as being implemented as part of the technology, it is understood that such values may be approximated, unless otherwise stated, and such values may be utilized to any suitable significant digit to the extent that a practical technical implementation may permit or require it.

Unless defined otherwise, all technical and scientific terms used herein have the same meaning as commonly understood by one of ordinary skill in the art to which this technology belongs. Although any methods and materials similar or equivalent to those described herein can also be used in the practice or testing of the present technology, a limited number of the exemplary methods and materials are described herein.

When a particular material is identified as being used to construct a component, obvious alternative materials with similar properties may be used as a substitute. Furthermore, unless specified to the contrary, any and all components herein described are understood to be capable of being manufactured and, as such, may be manufactured together or separately.

It must be noted that as used herein and in the appended claims, the singular forms “a”, “an”, and “the” include their plural equivalents, unless the context clearly dictates otherwise.

All publications mentioned herein are incorporated herein by reference in their entirety to disclose and describe the methods and/or materials which are the subject of those publications. The publications discussed herein are provided solely for their disclosure prior to the filing date of the present application. Nothing herein is to be construed as an admission that the present technology is not entitled to antedate such publication by virtue of prior invention. Further, the dates of publication provided may be different from the actual publication dates, which may need to be independently confirmed.

The terms “comprises” and “comprising” should be interpreted as referring to elements, components, or steps in a non-exclusive manner, indicating that the referenced elements, components, or steps may be present, or utilized, or combined with other elements, components, or steps that are not expressly referenced.

The subject headings used in the detailed description are included only for the ease of reference of the reader and should not be used to limit the subject matter found throughout the disclosure or the claims. The subject headings should not be used in construing the scope of the claims or the claim limitations.

Although the technology herein has been described with reference to particular examples, it is to be understood that these examples are merely illustrative of the principles and applications of the technology. In some instances, the terminology and symbols may imply specific details that are not required to practice the technology. For example, although the terms “first” and “second” may be used, unless otherwise specified, they are not intended to indicate any order but may be utilised to distinguish between distinct elements. Furthermore, although process steps in the methodologies may be described or illustrated in an order, such an ordering is not required. Those skilled in the art will recognize that such ordering may be modified and/or aspects thereof may be conducted concurrently or even synchronously.

It is therefore to be understood that numerous modifications may be made to the illustrative examples and that other arrangements may be devised without departing from the spirit and scope of the technology.

8 REFERENCE SIGNS LIST

| | |
|---|---|
| patient | 1000 |
| bed partner | 1100 |
| patient interface | 3000 |
| full face mask | 3010 |
| nasal cushion | 3020 |
| nasal pillows | 3030 |
| oro - nasal mask | 3040 |
| seal - forming structure | 3100 |
| elbow | 3160 |
| plenum chamber | 3200 |
| air entry port | 3210 |
| air entry port | 3220 |
| positioning and stabilising structure/conduit headgear | 3300 |
| left tube of conduit headgear | 3310 |
| right tube of conduit headgear | 3320 |
| strap | 3330 |
| attachment point | 3350 |
| crown connector | 3360 |
| rigid connector | 3370 |
| tab | 3380 |
| back strap | 3390 |
| vent structure | 3400 |
| plug structure | 3500 |
| connection port | 3600 |
| elbow | 3610 |
| adaptor | 3700 |
| adaptor swivel ring | 3710 |
| portion | 3715 |
| loop | 3716 |
| lid | 3720 |
| lid closure | 3720 |
| one - piece elbow | 3720 |
| adaptor elbow | 3722 |
| lid enclosure | 3720 |
| inner surface | 3721 |
| portion | 3730 |
| body | 3740 |
| slots | 3742 |
| opening | 3745 |
| raised mouth (or body) | 3746 |
| flanges | 3747 |
| track | 3750 |
| closure flap | 3760 |
| gap | 3765 |
| channels | 3766 |
| strut | 3770 |
| wedges | 3780 |
| closure | 3786 |
| ring | 3788 |
| hinge portion | 3789 |
| seal | 3790 |
| central aperture | 3795 |
| additional vent holes | 3799 |
| vent holes | 3799 |
| frame extension | 3800 |
| arms | 3810 |
| RPT device | 4000 |
| air circuit | 4170 |
| humidifier | 5000 |
| conduit headgear | 3300A |
| headstrap | 3300B |
| headstrap | 3300B |
| tubes | 3310A |
| inferior end of left tube | 3310A |
| inferior end of right tube | 3320A |
| vent structure | 3400A |
| connection port - conduit headgear | 3600A |
| connection port - patient interface | 3600B |

The invention claimed is:

1. A patient interface for delivery of a flow of pressurised air from an air circuit to an entrance of a patient’s airways, the patient interface comprising:

a plenum chamber;

a seal-forming structure provided to the plenum chamber;

a plurality of connection ports configured to receive the flow of air from the air circuit and to deliver the flow of air to the entrance of the patient’s airways via the seal-forming structure, the plurality of connection ports comprising a first connection port and a second connection port; and one or more positioning and stabilising structures configured to provide a force to hold the seal-forming structure in a therapeutically effective position on a patient’s head in use, wherein the patient interface is structured and arranged to be worn by the patient in a first use configuration and a second use configuration, wherein in the first use configuration, the air circuit is connected to the first connection port which is configured to, in use, be positioned superior to the patient’s otobasion superior and which is connected to ports on sides of the plenum chamber via first and second gas delivery tubes being constructed and arranged to, in use, contact at least a region of the patient's head superior to the patient's otobasion superior to position and stabilise the seal-forming structure in the therapeutically effective position, wherein in the second use configuration, the air circuit is connected to the second connection port which is configured to, in use, be positioned on an anterior side of the plenum chamber inferior to the patient's otobasion superior, and wherein, when the air circuit is connected to the first connection port in the first use configuration, the second connection port receives a vent structure or a stop.

2. The patient interface as claimed in claim 1, wherein the one or more positioning and stabilising structures comprises first and second positioning and stabilising structures configured to be interchangeably provided as part of the patient interface.

3. The patient interface as claimed in claim 2, wherein the first positioning and stabilising structure is configured for use with the patient interface in the first use configuration.

4. The patient interface as claimed in claim 2, wherein the first positioning and stabilising structure comprises the first and second gas delivery tubes being constructed and arranged to, in use, contact at least a region of the patient's head superior to the patient's otobasion superior, wherein a portion of the first and second gas delivery tubes configured to, in use, be positioned superior to the patient's otobasion superior is provided to the first connection port.

5. The patient interface as claimed in claim 4, wherein the first connection port is provided to the first positioning and stabilising structure, wherein the portion of the first and second gas delivery tubes configured to, in use, be positioned superior to the patient's otobasion superior is provided with the first connection port.

6. The patient interface as claimed in claim 2, wherein the second positioning and stabilising structure comprises one or more straps, constructed and arranged to, in use, contact at least a region of the patient's head superior to the patient's otobasion superior, wherein the second positioning and stabilising structure is configured for use with the patient interface in the second use configuration.

7. The patient interface as claimed in claim 1, wherein the first connection port is provided to a portion of the first and second gas delivery tubes configured to, in use, be positioned superior to the patient's otobasion superior.

8. The patient interface as claimed in claim 7, wherein the first and second connection ports are configured to be provided, respectively, with first and second closures.

9. The patient interface as claimed in claim 8, wherein the first and second closures are configured to be moveable from a closed condition to an open condition.

10. The patient interface as claimed in claim 9, wherein each of the first and second closures comprises an opening and at least one closure lid covering at least a portion of the opening when in the closed condition.

11. The patient interface as claimed in claim 10, wherein each of the first and second closures comprises a ring structure circumscribing the corresponding opening.

12. The patient interface as claimed in claim 11, wherein the at least one closure lid of the first closure and/or the at least one closure lid of the second closure are respectively pivotally hinged by an outer edge to a corresponding one of the ring structures.

13. The patient interface as claimed in claim 11, wherein the at least one closure lid of the first closure and/or the at least one closure lid of the second closure are slideably mounted to a corresponding one of the ring structures, wherein each ring structure is provided with a track along which the at least one closure lid is configured to slide.

14. The patient interface as claimed in claim 10, wherein the first closure and/or the second closure includes a vent.

15. The patient interface as claimed in claim 14, wherein the vent is in the form of one or more apertures provided to the at least one closure lid of the first closure and/or the at least one closure lid of the second closure.

16. The patient interface as claimed in claim 14, wherein the at least one closure lid of the first closure and/or the at least one closure lid of the second closure comprises two or more closure flaps, and wherein the vent is in the form of a slit formed by a distance between adjacent closure flaps.

17. The patient interface as claimed in claim 14, wherein the at least one closure lid of the first closure and/or the at least one closure lid of the second closure comprises four closure flaps attached to an inside surface of a corresponding one of the first closure or second closure, and wherein the vent is in the form of two intersecting slits formed by a distance between adjacent closure flaps.

18. The patient interface as claimed in claim 9, wherein the first closure and/or the second closure comprises an opening and at least one closure flap covering at least a portion of the opening when in the closed condition and arranged to be biased from the closed condition to the open condition by an end portion of the air circuit.

19. The patient interface as claimed in claim 18, wherein the first closure and/or the second closure comprises a ring structure circumscribing the opening.

20. The patient interface as claimed in claim 19, wherein the at least one closure flap of the first closure and/or the at least one closure flap of the second closure is pivotally hinged by an outer edge to the ring structure.

21. The patient interface as claimed in claim 19, wherein the at least one closure flap of the first closure and/or the at least one closure flap of the second closure is pivotally hinged to a strut spanning the opening of the ring.

22. The patient interface as claimed in claim 19, wherein the at least one closure flap of the first closure and/or the at least one closure flap of the second closure spans the corresponding opening or ring structure and is provided with a central aperture which increases in size as the first closure and/or second closure is biased from the closed condition to the open condition by the end portion of the air circuit.

23. The patient interface as claimed in claim 18, wherein the end portion of the air circuit includes an activation mechanism arranged to act against the first and second closures.

24. The patient interface as claimed in claim 8, wherein, when in an open condition the first closure and the second closure are configured to allow delivery of the flow of air to the entrance of the patient's airways, wherein, when in the first use configuration, the first closure of the first connection port is in the open condition and the second closure of the second connection port is in a closed condition, and wherein, when in the second use configuration, the first closure of the first connection port is in a closed condition and the second closure of the second connection port is in an open condition.

25. The patient interface as claimed in claim 1, wherein the patient interface further comprises one or more vent structures or stops.

26. The patient interface as claimed in claim 25, wherein each vent structure or stop is configured to connect to the first and/or second connection port.

27. The patient interface as claimed in claim 26, wherein, in the first use configuration, the air circuit is connected to the first connection port and one of the one or more vent structures or stops is connected to the second connection port, and, in the second use configuration, the air circuit is connected to the second connection port and one of the one or more vent structures or stops is connected to the first connection port.

28. The patient interface as claimed in claim 1, wherein the patient interface comprises more than one plenum chamber, wherein each plenum chamber is configured to be interchangeably comprised as part of the patient interface.

29. The patient interface as claimed in claim 1, wherein the patient interface comprises more than one seal-forming structure, wherein each seal-forming structure is configured to be interchangeably comprised as part of the patient interface.

30. The patient interface as claimed in claim 29, wherein the patient interface comprises more than one plenum chamber, wherein each plenum chamber is configured to be interchangeably comprised as part of the patient interface, and wherein the plenum chambers and/or seal-forming structures are configured as one or more of: a nasal mask, nasal cushion, nasal pillows or a full-face mask.

31. The patient interface as claimed in claim 1, wherein the one or more positioning and stabilising structures comprises first and second positioning and stabilising structures configured to be provided as part of the patient interface.

32. The patient interface as claimed in claim 31, wherein the first positioning and stabilising structure is configured to provide a force to hold the seal-forming structure in a therapeutically effective position on a patient's head in use, wherein the first positioning and stabilising structure includes the first and second gas delivery tubes being constructed and arranged to, in use, contact, in a first use configuration, at least a region of the patient's head superior to the patient's otobasion superior, wherein a portion of the first and second gas delivery tubes configured to, in use, be positioned superior to the patient's otobasion superior in the first use configuration is provided with the first connection port to receive the flow of air from the air circuit and to deliver the flow of air to the entrance of the patient's airways via the seal-forming structure, and wherein the first and second gas delivery tubes have respective inferior ends configured to be connected to a respective side of the plenum chamber.

33. The patient interface as claimed in claim 32, wherein the inferior ends of the first and second gas delivery tubes are connected to the sides of the plenum chamber in a manner such that the first positioning and stabilising structure is moveable between the first use configuration and the second use configuration.

34. The patient interface as claimed in claim 32, wherein, in the first use configuration, the first positioning and stabilising structure is configured to, in use, contact at least a region of the patient's head superior to the patient's otobasion superior and the first connection port receives the flow of air from the air circuit.

35. The patient interface as claimed in claim 32, wherein, in the second use configuration, the second positioning and stabilising structure is configured to, in use, contact at least a region of the patient's head superior to the patient's otobasion superior, and the second connection port is configured to receive the flow of air from the air circuit.

36. The patient interface as claimed in claim 31, wherein the second positioning and stabilising structure is configured to provide a force to hold the seal-forming structure in a therapeutically effective position on a patient's head in use, the second positioning and stabilising structure including at least one strap being constructed and arranged to contact, in a second use configuration, at least a region of the patient's head superior to the patient's otobasion superior.

37. A patient interface for delivery of a flow of pressurised air from an air circuit to an entrance of a patient's airways, the patient interface comprising:

a plenum chamber;

a seal-forming structure provided to the plenum chamber;

a first positioning and stabilising structure configured to provide a force to hold the seal-forming structure in a therapeutically effective position on a patient's head in use, wherein the first positioning and stabilising structure comprises at least one gas delivery tube constructed and arranged to contact, in a first use configuration, at least a region of the patient's head superior to the patient's otobasion superior, wherein a portion of the at least one gas delivery tube configured to, in use, be positioned superior to the patient's otobasion superior is provided with a first connection port to receive the flow of air from the air circuit and to deliver the flow of air to the entrance of the patient's airways via the seal-forming structure in the first use configuration, wherein the at least one gas delivery tube is connected, in the first use configuration, to a port on a side of the plenum chamber and is constructed and arranged to position and stabilise the seal-forming structure in the therapeutically effective position; and a second positioning and stabilising structure configured to provide a force to hold the seal-forming structure in the therapeutically effective position on the patient's head in use, wherein, in a second use configuration, the second positioning and stabilising structure is constructed and arranged to contact at least a region of the patient's head superior to the patient's otobasion superior;

a second connection port to receive the flow of air from the air circuit, wherein the second connection port is provided to an anterior side of the plenum chamber, wherein, in the second use configuration, the second connection port is configured to receive the flow of air from the air circuit to deliver the flow of air to the seal-forming structure in use; and a vent structure or stop configured to connect to the second connection port in the first use configuration.

38. The patient interface as claimed in claim 37, wherein the patient interface comprises more than one plenum chamber, wherein each plenum chamber is configured to be interchangeably comprised as part of the patient interface.

39. The patient interface as claimed in claim 37, wherein the patient interface comprises more than one seal-forming structure, wherein each seal-forming structure is configured to be interchangeably comprised as part of the patient interface.

40. The patient interface as claimed in claim 39, wherein the patient interface comprises more than one plenum chamber, wherein each plenum chamber is configured to be interchangeably comprised as part of the patient interface, and wherein the plenum chambers and/or seal-forming structures are configured as one or more of: a nasal mask, nasal cushion, nasal pillows or a full-face mask.

41. A patient interface for delivery of a flow of pressurised air to an entrance of a patient's airways, the patient interface comprising:

a plenum chamber;

a seal-forming structure provided to the plenum chamber; and a positioning and stabilising structure configured to provide a force to hold the seal-forming structure in a therapeutically effective position on a patient's head in use, wherein the positioning and stabilising structure includes at least one gas delivery tube constructed and arranged to contact at least a region of the patient's head superior to the patient's otobasion superior, wherein a portion of the at least one gas delivery tube configured to, in use, be positioned superior to the patient's otobasion superior is provided with a first connection port to, in a first use configuration, receive the flow of air from an air circuit and to deliver the flow of air to the entrance of the patient's airways via the seal-forming structure, and wherein the at least one gas delivery tube is connected, in the first use configuration, to a port on a side of the plenum chamber and is constructed and arranged to position and stabilise the seal-forming structure in the therapeutically effective position, wherein an anterior side of the plenum chamber is provided with a second connection port to, in a second use configuration, receive the flow of air from the air circuit and to deliver the flow of air to the entrance of the patient's airways via the seal-forming structure, and wherein the patient interface further comprises one or more vent structures or stops, each vent structure or stop configured to connect to the first and/or second connection port, and wherein, in the first use configuration, the air circuit is connected to the first connection port and one of the one or more vent structures or stops is connected to the second connection port, and, in the second use configuration, the air circuit is connected to the second connection port and one of the one or more vent structures or stops is connected to the first connection port.

42. A patient interface for delivery of a flow of pressurised air from an air circuit to an entrance of a patient's airways, the patient interface comprising:

a plenum chamber;

a seal-forming structure provided to the plenum chamber; and a first positioning and stabilising structure configured to provide a force to hold the seal-forming structure in a therapeutically effective position on a patient's head in use, wherein the first positioning and stabilising structure includes at least one gas delivery tube constructed and arranged to contact, in a first use configuration, at least a region of the patient's head superior to the patient's otobasion superior, wherein a portion of the gas delivery tube configured to, in use, be positioned superior to the patient's otobasion superior in the first use configuration is provided with a connection port to receive the flow of air from the air circuit and to deliver the flow of air to the entrance of the patient's airways via the seal-forming structure, and wherein the at least one gas delivery tube has an inferior end configured to be connected to a side of the plenum chamber and constructed and arranged to position and stabilise the seal-forming structure in the therapeutically effective position in the first use configuration; and a second positioning and stabilising structure configured to provide a force to hold the seal-forming structure in a therapeutically effective position on a patient's head in use, the second positioning and stabilising structure including at least one strap constructed and arranged to be connected to headgear attachment points of the plenum chamber and to contact, in a second use configuration, at least a region of the patient's head superior to the patient's otobasion superior in use, wherein the second positioning and stabilising structure is selectively provided as part of the patient interface such that, in the first use configuration, the at least one strap is not connected to the headgear attachment points and is not configured to contact the patient's head in use, wherein the inferior end of the at least one gas delivery tube is configured to connect to the side of the plenum chamber in a manner such that the first positioning and stabilising structure is moveable between a first orientation in the first use configuration and a second orientation in the second use configuration, and wherein in the second use configuration, the connection port is configured to be positioned inferior to the patient's otobasion superior in use.

43. A patient interface for delivery of a flow of pressurised air to an entrance of a patient's airways, the patient interface comprising:

a plenum chamber;

a seal-forming structure provided to the plenum chamber; and a positioning and stabilising structure configured to provide a force to hold the seal-forming structure in a therapeutically effective position on a patient's head in use, wherein the positioning and stabilising structure includes at least one gas delivery tube constructed and arranged to contact at least a region of the patient's head superior to the patient's otobasion superior, wherein a portion of the at least one gas delivery tube configured to, in use, be positioned superior to the patient's otobasion superior is provided with a first connection port to, in a first use configuration, receive the flow of air from an air circuit and to deliver the flow of air to the entrance of the patient's airways via the seal-forming structure, and wherein the at least one gas delivery tube is connected, in the first use configuration, to a port on a side of the plenum chamber and is constructed and arranged to position and stabilise the seal-forming structure in the therapeutically effective position, wherein an anterior side of the plenum chamber is provided with a second connection port to, in a second use configuration, receive the flow of air from the air circuit and deliver the flow of air to the entrance of the patient's airways via the seal-forming structure, and wherein the first and second connection ports are each configured with a respective closure, wherein each closure is arranged to be moveable from a closed condition to an open condition, wherein, when in the open condition each closure allows delivery of the flow of air to the entrance of the patient's airways, and wherein, when in the first use configuration, the closure of the first connection port is in an open condition and the closure of the second connection port is in a closed condition, and wherein, when in the second use configuration, the closure of the first connection port is in a closed condition and the closure of the second connection port is in an open condition.

* * * * *